US008348998B2

(12) United States Patent
Pintor et al.

(10) Patent No.: US 8,348,998 B2
(45) Date of Patent: Jan. 8, 2013

(54) UNITARY QUICK CONNECT PROSTHETIC HEART VALVE AND DEPLOYMENT SYSTEM AND METHODS

(75) Inventors: Rafael Pintor, Mission Viejo, CA (US); Mark Chau, Aliso Viejo, CA (US); Travis Oba, Corona, CA (US); August Yambao, Temecula, CA (US); Louis A. Campbell, Santa Ana, CA (US); Tammy Huntley, Foothill Ranch, CA (US); Qinggang Zeng, Irvine, CA (US); Carey Cristea, Irvine, CA (US); Faisal Kalam, Corona, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 208 days.

(21) Appl. No.: 12/821,628

(22) Filed: Jun. 23, 2010

(65) Prior Publication Data

US 2010/0331972 A1 Dec. 30, 2010

Related U.S. Application Data

(60) Provisional application No. 61/220,968, filed on Jun. 26, 2009.

(51) Int. Cl.
*A61F 2/24* (2006.01)
(52) U.S. Cl. ............... 623/2.11; 623/1.11; 623/1.24; 623/1.26
(58) Field of Classification Search ............... None
See application file for complete search history.

(56) References Cited

U.S. PATENT DOCUMENTS

| | | | |
|---|---|---|---|
| 3,143,742 A | 8/1964 | Cromie |
| 3,320,972 A | 5/1967 | High |
| 3,371,352 A | 3/1968 | Siposs et al. |
| 3,409,013 A | 11/1968 | Henry |
| 3,546,710 A | 12/1970 | Ivanovich et al. |
| 3,574,865 A | 4/1971 | Hamaker |

(Continued)

FOREIGN PATENT DOCUMENTS

EP 84395 7/1983

(Continued)

OTHER PUBLICATIONS

International Search Report from corresponding PCT case No. PCT/US2009/068693 dated Aug. 17, 2010.

(Continued)

*Primary Examiner* — Corrine M McDermott
*Assistant Examiner* — Todd J Scherbel
(74) *Attorney, Agent, or Firm* — AnneMarie Kaiser; Guy Cumberbatch

(57) ABSTRACT

A quick-connect heart valve prosthesis that can be quickly and easily implanted during a surgical procedure is provided. The heart valve includes a substantially non-expandable, non-compressible prosthetic valve and a plastically-expandable coupling stent, thereby enabling attachment to the annulus without sutures. A small number of guide sutures may be provided for aortic valve orientation. The prosthetic valve may be a commercially available valve with a sewing ring with the coupling stent attached thereto. The coupling stent may expand from a conical deployment shape to a conical expanded shape, and may include web-like struts connected between axially-extending posts. A system and method for deployment includes a hollow two-piece handle through which a balloon catheter passes. A valve holder is stored with the heart valve and the handle easily attaches thereto to improve valve preparation steps.

28 Claims, 28 Drawing Sheets

U.S. PATENT DOCUMENTS

| | | |
|---|---|---|
| 3,628,535 A | 12/1971 | Ostrowsky et al. |
| 3,657,744 A | 4/1972 | Ersek |
| 3,686,740 A | 8/1972 | Shiley |
| 3,755,823 A | 9/1973 | Hancock |
| 3,839,741 A | 10/1974 | Haller |
| 3,997,923 A | 12/1976 | Possis |
| 4,035,849 A | 7/1977 | Angell |
| 4,078,468 A | 3/1978 | Civitello |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,217,665 A | 8/1980 | Bex |
| 4,218,782 A | 8/1980 | Rygg |
| 4,259,753 A | 4/1981 | Liotta et al. |
| RE30,912 E | 4/1982 | Hancock |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier |
| 4,470,157 A | 9/1984 | Love |
| 4,501,030 A | 2/1985 | Lane |
| 4,506,394 A | 3/1985 | Bedard |
| 4,535,483 A | 8/1985 | Klawitter et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,702,250 A | 10/1987 | Ovil et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,865,600 A | 9/1989 | Carpentier et al. |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,147,391 A | 9/1992 | Lane |
| 5,163,955 A | 11/1992 | Love et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,370,685 A | 12/1994 | Stevens |
| 5,376,112 A | 12/1994 | Duran |
| 5,396,887 A | 3/1995 | Imran |
| 5,397,351 A | 3/1995 | Pavcnik et al. |
| 5,411,522 A | 5/1995 | Trott |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,476,510 A | 12/1995 | Eberhardt et al. |
| 5,488,789 A | 2/1996 | Religa et al. |
| 5,489,297 A | 2/1996 | Duran |
| 5,489,298 A | 2/1996 | Love et al. |
| 5,500,016 A | 3/1996 | Fisher |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,776,187 A | 7/1998 | Krueger et al. |
| 5,776,188 A | 7/1998 | Shepherd et al. |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,865,801 A | 2/1999 | Houser |
| 5,891,160 A | 4/1999 | Williamson et al. |
| 5,895,420 A | 4/1999 | Mirsch et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,957,949 A | 9/1999 | Leonhardt et al. |
| 5,972,004 A | 10/1999 | Williamson et al. |
| 5,984,959 A | 11/1999 | Robertson et al. |
| 5,984,973 A | 11/1999 | Girard et al. |
| 6,010,531 A | 1/2000 | Donlon et al. |
| 6,042,607 A | 3/2000 | Williamson, IV et al. |
| 6,059,827 A | 5/2000 | Fenton, Jr. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward |
| 6,106,550 A | 8/2000 | Magovern et al. |
| 6,110,200 A | 8/2000 | Hinnenkamp |
| 6,117,091 A | 9/2000 | Young et al. |
| 6,162,233 A | 12/2000 | Williamson, IV et al. |
| 6,168,614 B1 | 1/2001 | Andersen et al. |
| 6,176,877 B1 | 1/2001 | Buchanan et al. |
| 6,197,054 B1 | 3/2001 | Hamblin, Jr. et al. |
| 6,217,611 B1 | 4/2001 | Klostermeyer |
| 6,231,561 B1 | 5/2001 | Frazier et al. |
| 6,241,765 B1 | 6/2001 | Griffin et al. |
| 6,245,102 B1 | 6/2001 | Jayaraman |
| 6,283,127 B1 | 9/2001 | Sterman et al. |
| 6,287,339 B1 | 9/2001 | Vazquez et al. |
| 6,290,674 B1 | 9/2001 | Roue et al. |
| 6,312,447 B1 | 11/2001 | Grimes |
| 6,312,465 B1 | 11/2001 | Griffin et al. |
| 6,328,727 B1 | 12/2001 | Frazier et al. |
| 6,371,983 B1 | 4/2002 | Lane |
| 6,402,780 B2 | 6/2002 | Williamson |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,468,305 B1 | 10/2002 | Otte |
| 6,530,952 B2 | 3/2003 | Vesely |
| 6,558,429 B2 | 5/2003 | Taylor |
| 6,569,196 B1 | 5/2003 | Vesely |
| 6,582,462 B1 | 6/2003 | Andersen et al. |
| 6,585,766 B1 | 7/2003 | Huynh et al. |
| 6,652,578 B2 | 11/2003 | Bailey et al. |
| 6,682,559 B2 | 1/2004 | Myers et al. |
| 6,685,739 B2 | 2/2004 | DiMatteo et al. |
| 6,719,789 B2 | 4/2004 | Cox |
| 6,730,118 B2 | 5/2004 | Spenser et al. |
| 6,733,525 B2 | 5/2004 | Yang et al. |
| 6,764,508 B1 | 7/2004 | Roehe et al. |
| 6,767,362 B2 | 7/2004 | Schreck |
| 6,786,925 B1 | 9/2004 | Schoon et al. |
| 6,790,229 B1 | 9/2004 | Berreklouw |

| | | |
|---|---|---|
| 6,790,230 B2 | 9/2004 | Beyersdorf et al. |
| 6,805,711 B2 | 10/2004 | Quijano et al. |
| 6,846,325 B2 | 1/2005 | Liddicoat |
| 6,893,459 B1 | 5/2005 | Macoviak |
| 6,893,460 B2 | 5/2005 | Spenser et al. |
| 6,908,481 B2 | 6/2005 | Cribier |
| 6,936,067 B2 | 8/2005 | Buchanan |
| 6,939,365 B1 | 9/2005 | Fogarty et al. |
| 6,964,682 B2 * | 11/2005 | Nguyen-Thien-Nhon et al. ............ 623/2.11 |
| 6,974,476 B2 | 12/2005 | McGuckin, Jr. et al. |
| 6,978,176 B2 * | 12/2005 | Lattouf .................. 607/9 |
| 7,011,681 B2 | 3/2006 | Vesely |
| 7,018,406 B2 | 3/2006 | Seguin et al. |
| 7,025,780 B2 | 4/2006 | Gabbay |
| 7,070,616 B2 | 7/2006 | Majercak et al. |
| 7,081,131 B2 | 7/2006 | Thornton |
| 7,097,659 B2 | 8/2006 | Woolfson et al. |
| 7,101,396 B2 | 9/2006 | Artof et al. |
| 7,147,663 B1 | 12/2006 | Berg et al. |
| 7,153,324 B2 | 12/2006 | Case et al. |
| 7,160,320 B2 * | 1/2007 | Duran ............ 623/1.24 |
| 7,172,625 B2 | 2/2007 | Shu et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,252,682 B2 | 8/2007 | Seguin |
| 7,261,732 B2 | 8/2007 | Justino |
| 7,311,730 B2 | 12/2007 | Gabbay |
| RE40,377 E | 6/2008 | Williamson, IV et al. |
| 7,422,603 B2 | 9/2008 | Lane |
| 7,429,269 B2 | 9/2008 | Schwammenthal et al. |
| 7,442,204 B2 | 10/2008 | Schwammenthal et al. |
| 7,445,630 B2 | 11/2008 | Lashinski et al. |
| 7,468,073 B2 | 12/2008 | Johnson et al. |
| 7,470,285 B2 | 12/2008 | Nugent et al. |
| 7,510,575 B2 * | 3/2009 | Spenser et al. ........ 623/2.18 |
| 7,513,909 B2 | 4/2009 | Lane et al. |
| 7,534,261 B2 | 5/2009 | Fiedman |
| 7,556,647 B2 | 7/2009 | Drews et al. |
| 7,569,072 B2 | 8/2009 | Berg et al. |
| 7,578,843 B2 | 8/2009 | Shu |
| 7,585,321 B2 | 9/2009 | Cribier |
| 7,597,711 B2 | 10/2009 | Drews et al. |
| 7,611,535 B2 | 11/2009 | Woolfson et al. |
| 7,658,763 B2 * | 2/2010 | Stobie .............. 623/2.11 |
| 7,682,390 B2 | 3/2010 | Seguin |
| 7,708,775 B2 * | 5/2010 | Rowe et al. ............ 623/2.11 |
| 8,167,932 B2 * | 5/2012 | Bourang et al. ........ 623/2.11 |
| 2001/0021872 A1 | 9/2001 | Bailey et al. |
| 2001/0039435 A1 | 11/2001 | Roue et al. |
| 2001/0039436 A1 | 11/2001 | Fraizer et al. |
| 2001/0041914 A1 | 11/2001 | Fraizer et al. |
| 2001/0041915 A1 | 11/2001 | Roue et al. |
| 2001/0049492 A1 | 12/2001 | Frazier et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0236568 A1 | 12/2003 | Hojeibane |
| 2004/0019374 A1 | 1/2004 | Hojeibane et al. |
| 2004/0034411 A1 | 2/2004 | Quijano |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson, IV et al. |
| 2004/0186563 A1 | 9/2004 | Lobbi |
| 2004/0186565 A1 * | 9/2004 | Schreck .................. 623/2.18 |
| 2004/0193261 A1 | 9/2004 | Berreklouw |
| 2004/0206363 A1 | 10/2004 | McCarthy |
| 2004/0210304 A1 | 10/2004 | Seguin et al. |
| 2004/0210307 A1 | 10/2004 | Khairkhahan |
| 2004/0225355 A1 | 11/2004 | Stevens |
| 2004/0236411 A1 | 11/2004 | Sarac |
| 2004/0260389 A1 | 12/2004 | Case et al. |
| 2004/0260390 A1 | 12/2004 | Sarac |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137695 A1 | 6/2005 | Salahieh et al. |
| 2005/0137702 A1 | 6/2005 | Haug et al. |
| 2005/0159811 A1 | 7/2005 | Lane |
| 2005/0165477 A1 | 7/2005 | Anduiza et al. |
| 2005/0165479 A1 | 7/2005 | Drews et al. |
| 2005/0182483 A1 | 8/2005 | Osborne et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240259 A1 | 10/2005 | Sisken et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0122692 A1 | 6/2006 | Gilad et al. |
| 2006/0136054 A1 | 6/2006 | Berg et al. |
| 2006/0149360 A1 | 7/2006 | Schwammenthal et al. |
| 2006/0154230 A1 | 7/2006 | Cunanan et al. |
| 2006/0161249 A1 | 7/2006 | Realyvasquez et al. |
| 2006/0167543 A1 | 7/2006 | Bailey et al. |
| 2006/0195183 A1 | 8/2006 | Navia et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0229708 A1 | 10/2006 | Powell et al. |
| 2006/0235508 A1 | 10/2006 | Lane et al. |

| | | | | | | |
|---|---|---|---|---|---|---|
| 2006/0241745 | A1 | 10/2006 | Solem | 2010/0161036 A1* | 6/2010 | Pintor et al. .................. 623/1.26 |
| 2006/0246888 | A1 | 11/2006 | Bender et al. | 2010/0249894 A1* | 9/2010 | Oba et al. ...................... 623/1.11 |
| 2006/0253191 | A1 | 11/2006 | Salahieh et al. | 2010/0249908 A1* | 9/2010 | Chau et al. .................... 623/1.26 |
| 2006/0259134 | A1 | 11/2006 | Schwammenthal et al. | 2011/0147251 A1* | 6/2011 | Hodshon et al. ............... 206/438 |
| 2006/0259135 | A1 | 11/2006 | Navia et al. | 2012/0065729 A1* | 3/2012 | Pintor et al. .................. 623/2.11 |
| 2006/0259136 | A1 | 11/2006 | Nguyen et al. | 2012/0150288 A1* | 6/2012 | Hodshon et al. ............... 623/2.11 |
| 2006/0265056 | A1 | 11/2006 | Nguyen et al. | | | |
| 2006/0271172 | A1 | 11/2006 | Tehrani | | | |

FOREIGN PATENT DOCUMENTS

| | | |
|---|---|---|
| EP | 96721 | 12/1983 |
| EP | 125393 | 11/1984 |
| EP | 143246 | 6/1985 |
| EP | 179562 | 4/1986 |
| EP | 1171059 | 6/2002 |
| GB | 2056023 | 3/1981 |
| GB | 2069843 | 9/1981 |
| GB | 2254254 | 10/1992 |
| GB | 2279134 | 12/1994 |
| SU | 1116573 | 7/1985 |
| SU | 1697790 | 12/1991 |
| WO | 8900840 | 2/1989 |
| WO | 9115167 | 10/1991 |
| WO | 9212690 | 8/1992 |
| WO | 9213502 | 8/1992 |
| WO | 9219184 | 11/1992 |
| WO | 9219185 | 11/1992 |
| WO | 9517139 | 6/1995 |
| WO | 9528899 | 11/1995 |
| WO | 9640006 | 12/1996 |
| WO | 9727799 | 1/1997 |
| WO | 9709933 | 3/1997 |
| WO | 9709944 | 3/1997 |
| WO | 9741801 | 11/1997 |
| WO | 9742871 | 11/1997 |
| WO | 9806329 | 2/1998 |
| WO | 9911201 | 3/1999 |
| WO | 9915112 | 4/1999 |
| WO | 9951169 | 10/1999 |
| WO | 0032105 | 6/2000 |
| WO | 0040176 | 7/2000 |
| WO | 0060995 | 10/2000 |
| WO | 0154625 | 2/2001 |
| WO | 0154624 | 8/2001 |
| WO | 02076347 | 10/2002 |
| WO | 2006086135 | 8/2006 |

| | | | | |
|---|---|---|---|---|
| 2006/0271175 | A1 | 11/2006 | Woolfson et al. |
| 2006/0287717 | A1 | 12/2006 | Rowe et al. |
| 2006/0287719 | A1 | 12/2006 | Rowe et al. |
| 2007/0005129 | A1 | 1/2007 | Damm et al. |
| 2007/0010876 | A1 | 1/2007 | Salahieh et al. |
| 2007/0010877 | A1 | 1/2007 | Salahieh et al. |
| 2007/0016285 | A1 | 1/2007 | Lane et al. |
| 2007/0016286 | A1 | 1/2007 | Herrmann et al. |
| 2007/0016288 | A1 | 1/2007 | Gurskis et al. |
| 2007/0043435 | A1 | 2/2007 | Seguin et al. |
| 2007/0078509 | A1 | 4/2007 | Lotfy |
| 2007/0078510 | A1 | 4/2007 | Ryan |
| 2007/0100440 | A1 | 5/2007 | Figulla et al. |
| 2007/0129794 | A1 | 6/2007 | Realyvasquez |
| 2007/0142906 | A1 | 6/2007 | Figulla et al. |
| 2007/0142907 | A1 | 6/2007 | Moaddeb et al. |
| 2007/0150053 | A1 | 6/2007 | Gurskis et al. |
| 2007/0156233 | A1 | 7/2007 | Kapadia et al. |
| 2007/0162103 | A1 | 7/2007 | Case et al. |
| 2007/0162107 | A1 | 7/2007 | Haug et al. |
| 2007/0162111 | A1 | 7/2007 | Fukamachi et al. |
| 2007/0179604 | A1 | 8/2007 | Lane |
| 2007/0185565 | A1 | 8/2007 | Schwammenthal et al. |
| 2007/0198097 | A1 | 8/2007 | Zegdi |
| 2007/0203575 | A1 | 8/2007 | Forster et al. |
| 2007/0203576 | A1 | 8/2007 | Lee et al. |
| 2007/0213813 | A1 | 9/2007 | Von Segesser et al. |
| 2007/0225801 | A1 | 9/2007 | Drews et al. |
| 2007/0233237 | A1 | 10/2007 | Krivoruchko |
| 2007/0239266 | A1 | 10/2007 | Birdsall |
| 2007/0239269 | A1 | 10/2007 | Dolan et al. |
| 2007/0239273 | A1 | 10/2007 | Allen |
| 2007/0244558 | A1 | 10/2007 | Machiraju |
| 2007/0255398 | A1 | 11/2007 | Yang et al. |
| 2007/0260305 | A1 | 11/2007 | Drews et al. |
| 2007/0265701 | A1 | 11/2007 | Gurskis |
| 2007/0270944 | A1 | 11/2007 | Bergheim et al. |
| 2007/0282436 | A1 | 12/2007 | Pinchuk |
| 2007/0288089 | A1 | 12/2007 | Gurskis et al. |
| 2008/0021546 | A1 | 1/2008 | Patz et al. |
| 2008/0033543 | A1 | 2/2008 | Gurskis et al. |
| 2008/0065198 | A1 | 3/2008 | Quintessenza |
| 2008/0119875 | A1 | 5/2008 | Ino et al. |
| 2008/0281411 | A1 | 11/2008 | Berreklouw |
| 2008/0319543 | A1 | 12/2008 | Lane |
| 2009/0036903 | A1 | 2/2009 | Ino et al. |
| 2009/0192599 | A1 | 7/2009 | Lane et al. |
| 2009/0192602 | A1 | 7/2009 | Kuehn |
| 2009/0192603 | A1 | 7/2009 | Ryan |
| 2009/0192604 | A1 | 7/2009 | Gloss |
| 2009/0192605 | A1 | 7/2009 | Gloss et al. |
| 2009/0192606 | A1 | 7/2009 | Gloss et al. |

OTHER PUBLICATIONS

Krakow, "3F Therapeutics, Inc. Announces the First Clinical Implantation of the 3F Enable Aortic Heart Valve™, a Patented, Sutureless Implantation, Replacement Heart Valve Intended to Save Valuable Surgery Time and Reduce Time Related Complications . . . " Healthcare Sales & Marketing Network News Feed, Jan. 18, 2005, pp. 1-2.

Sadowski, Jerzy; Kapelak, Boguslaw; Bartus, Krzysztof, "Sutureless Heart Valve Implantation—A Case Study," Touch Briefings, 2005, pp. 48-50.

* cited by examiner

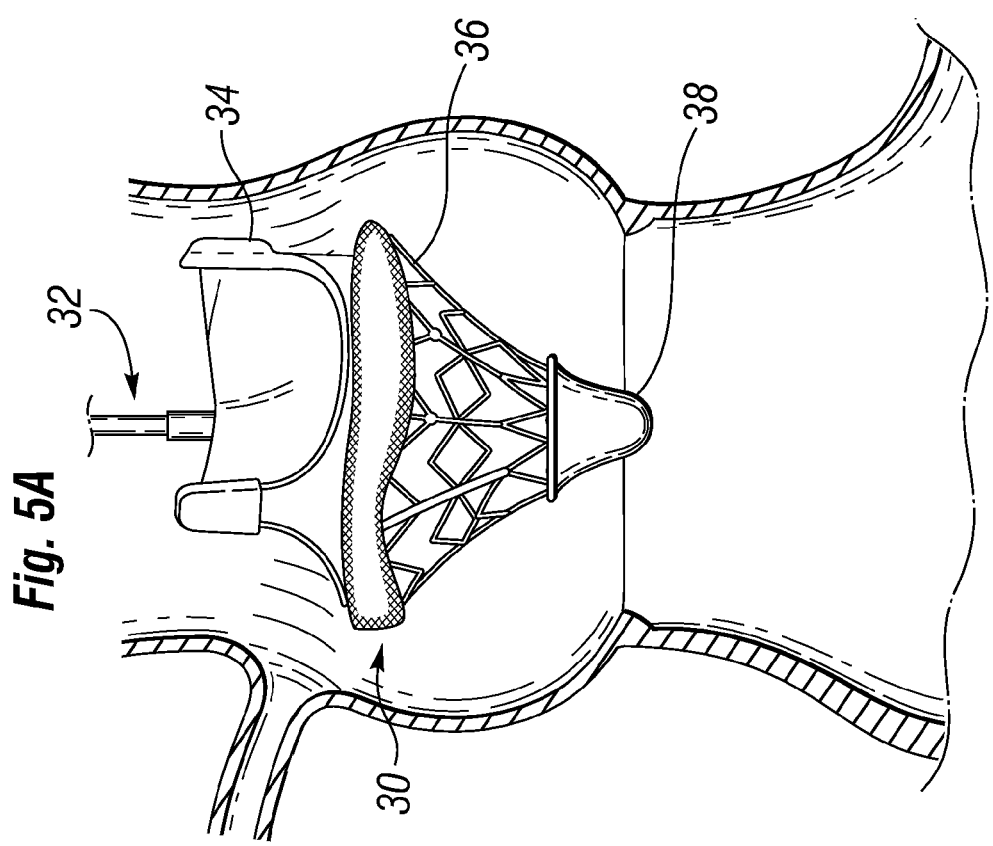

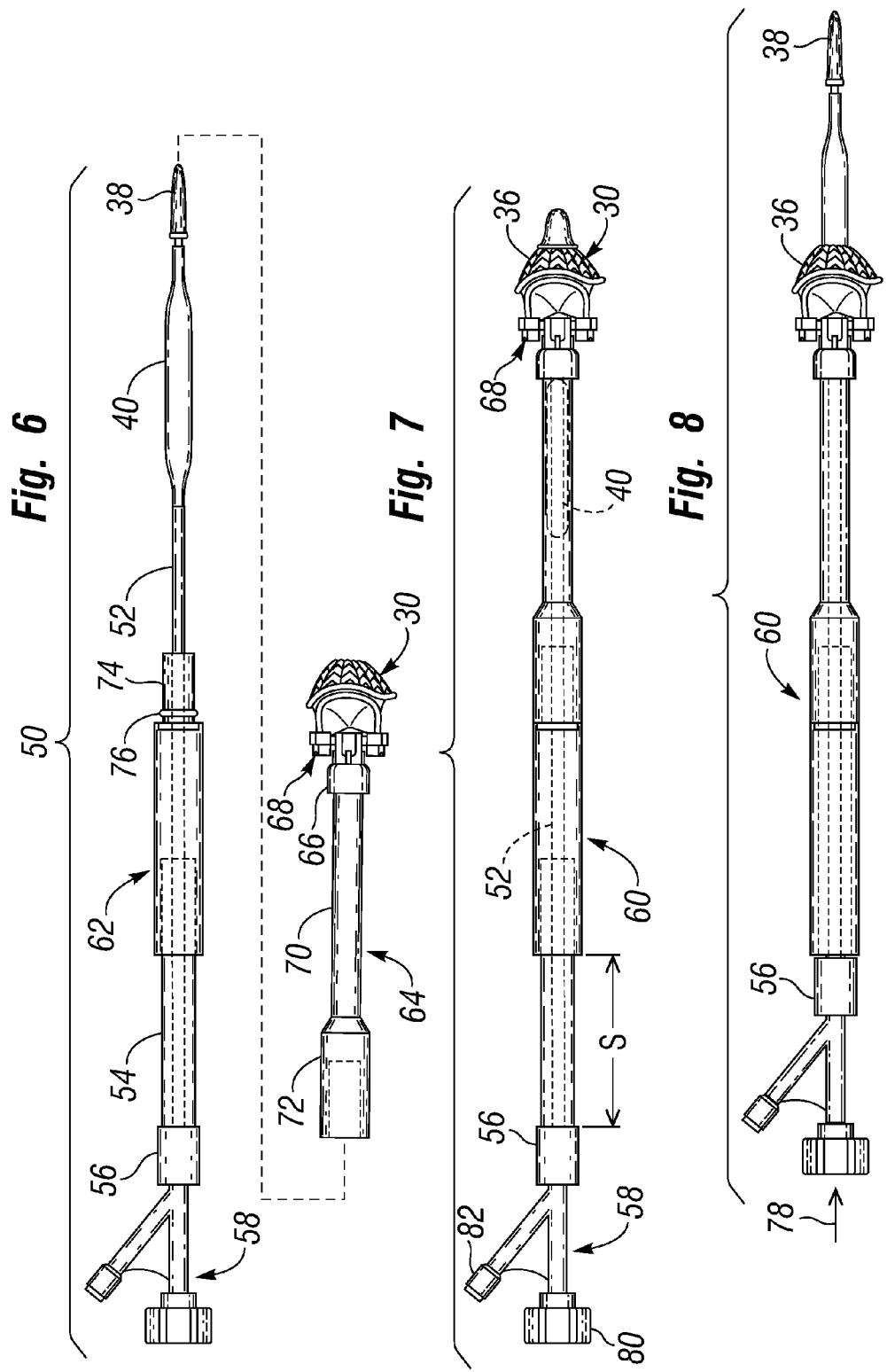

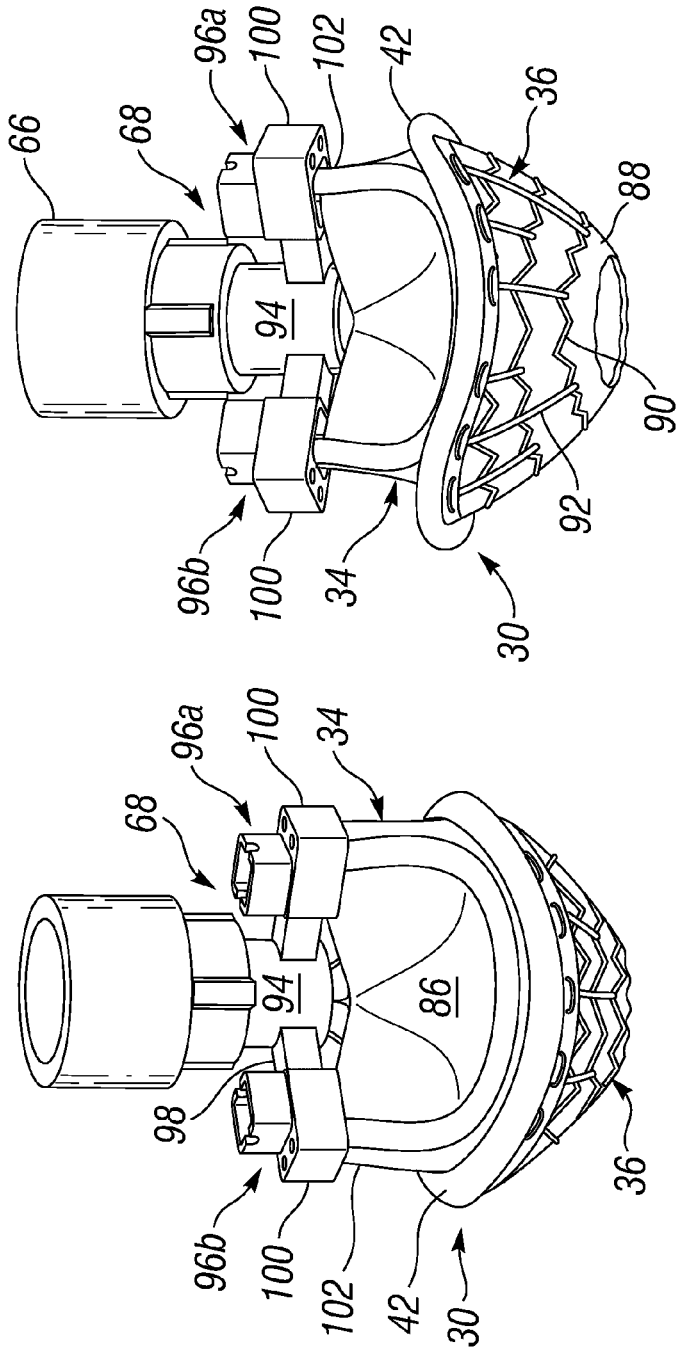

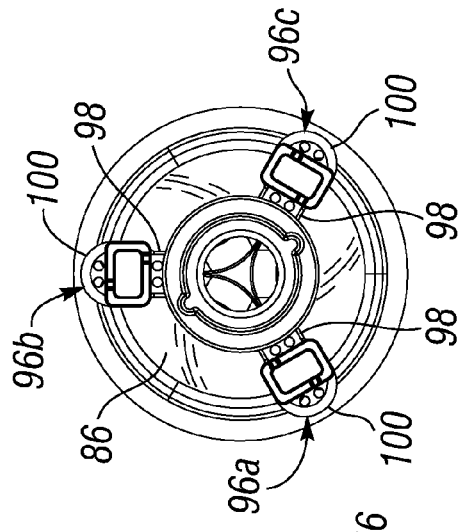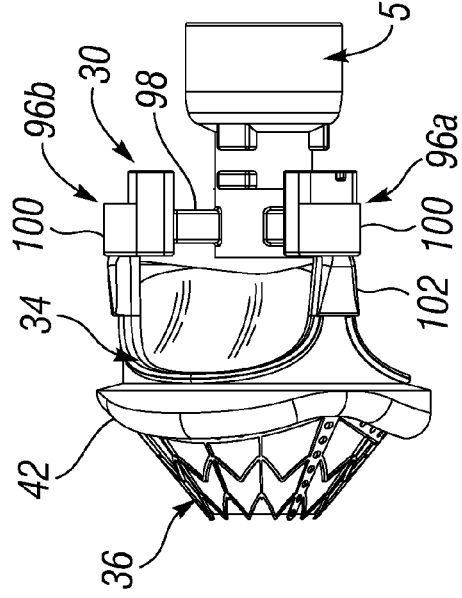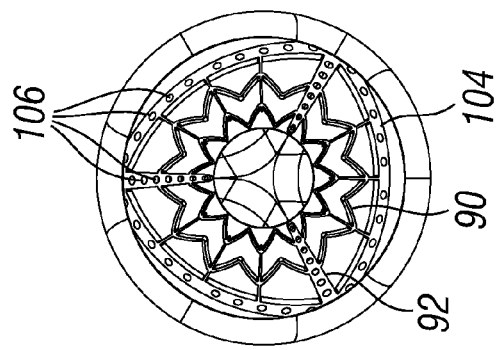

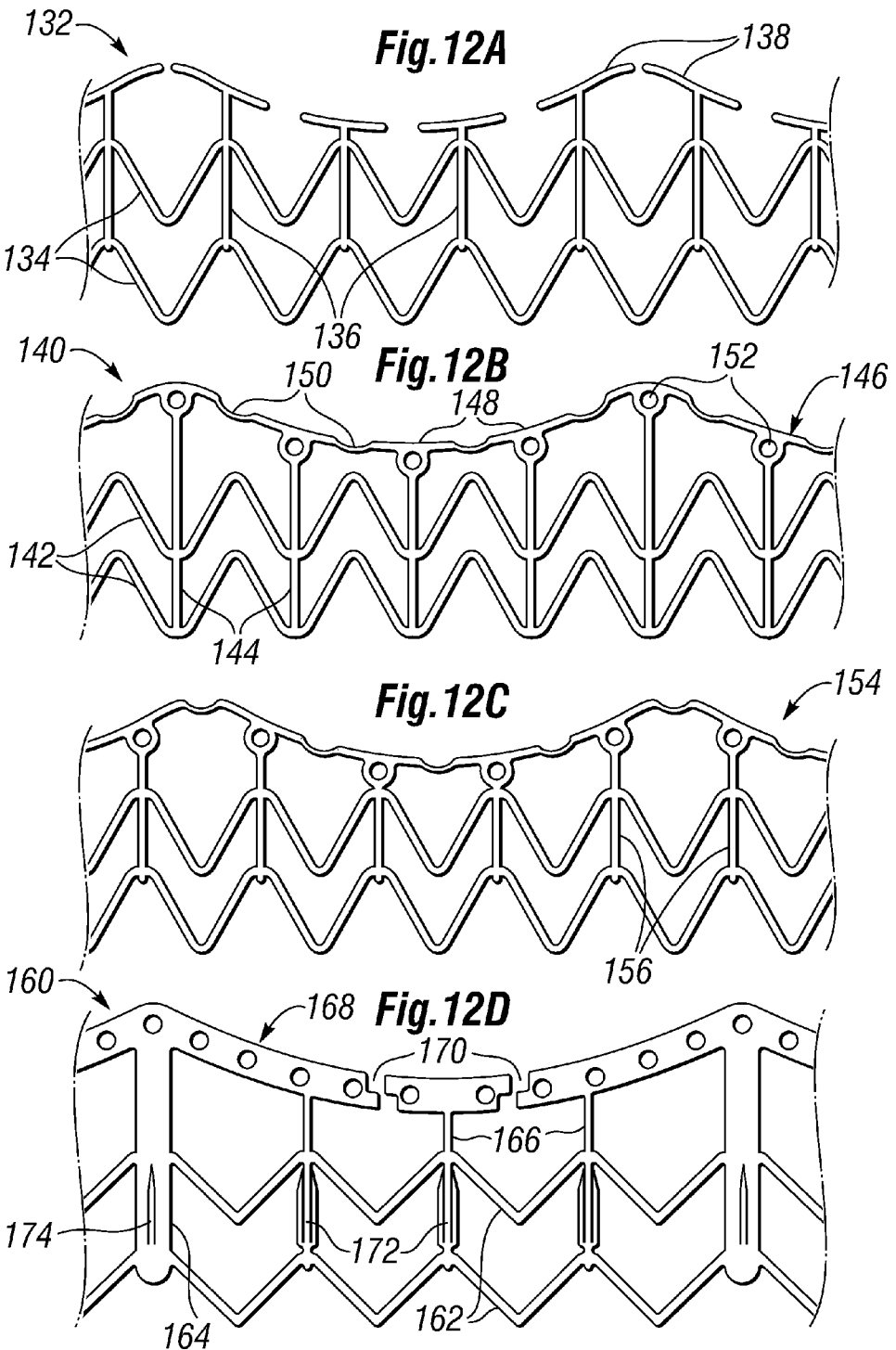

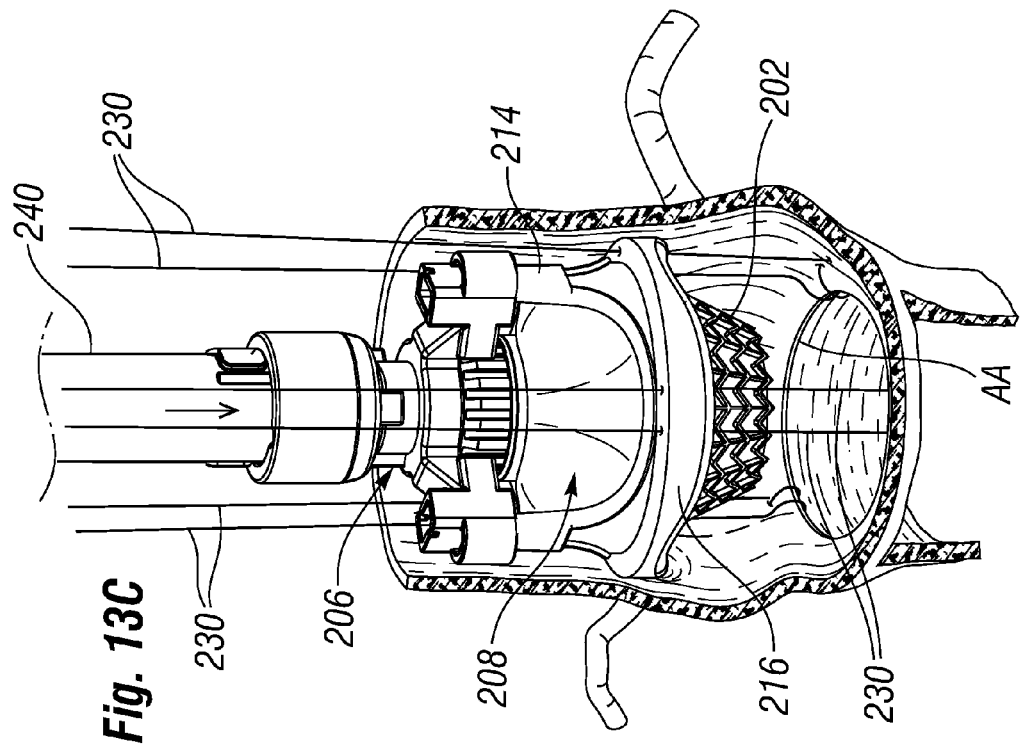
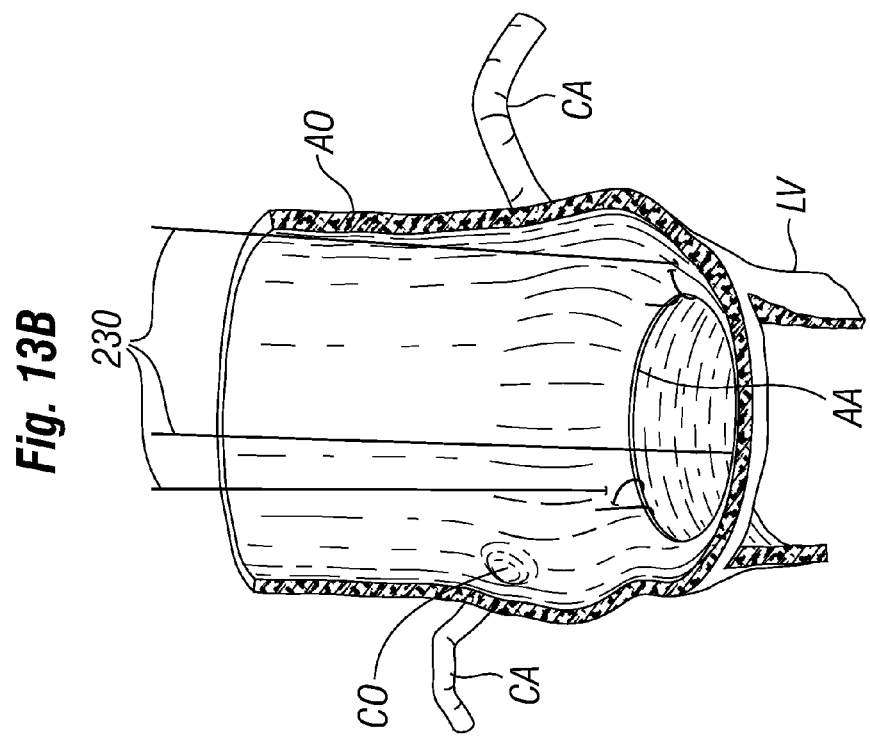

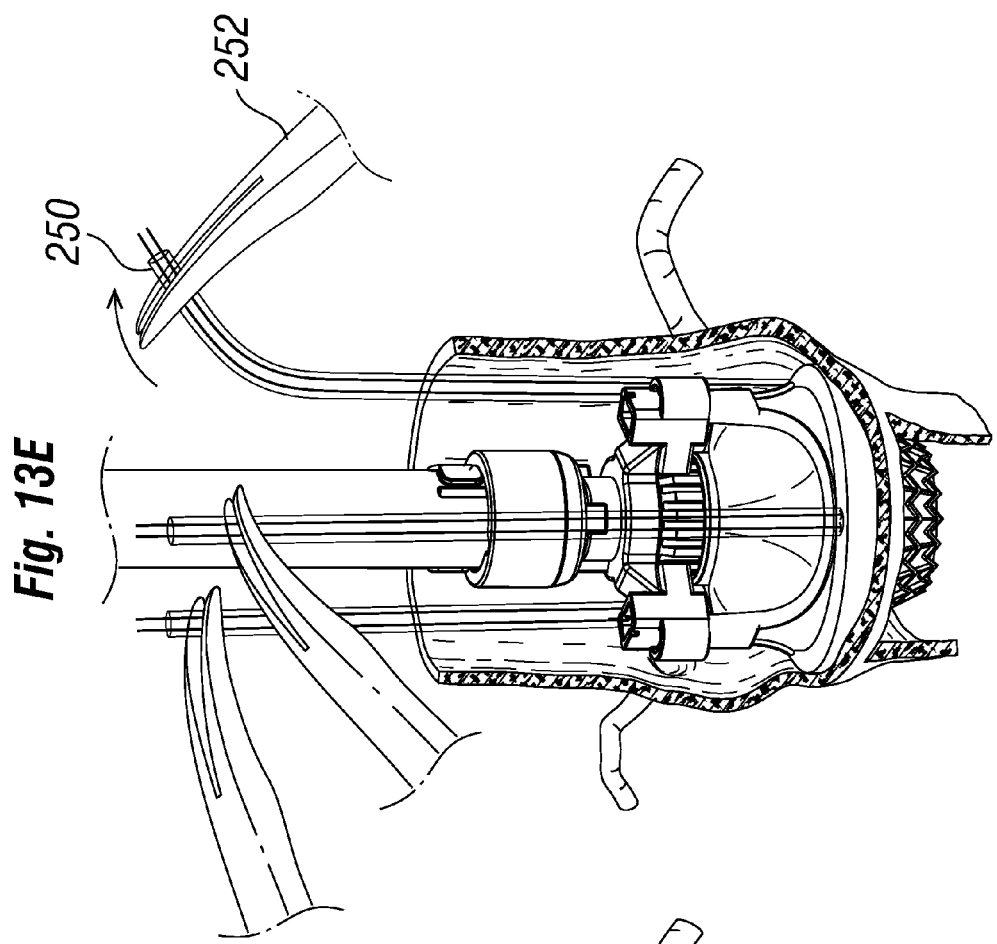
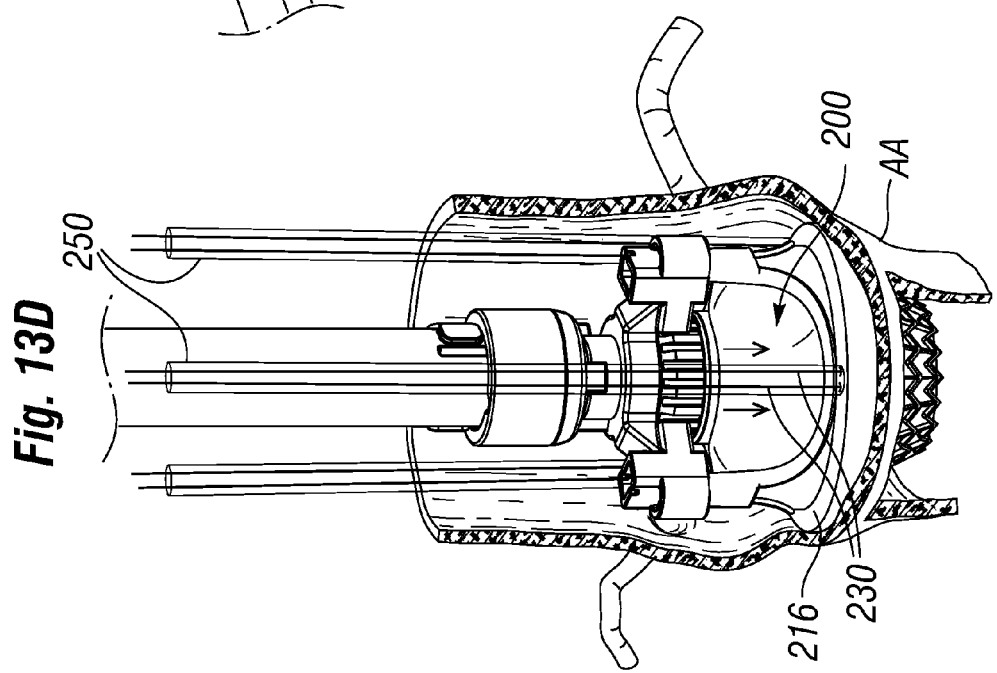

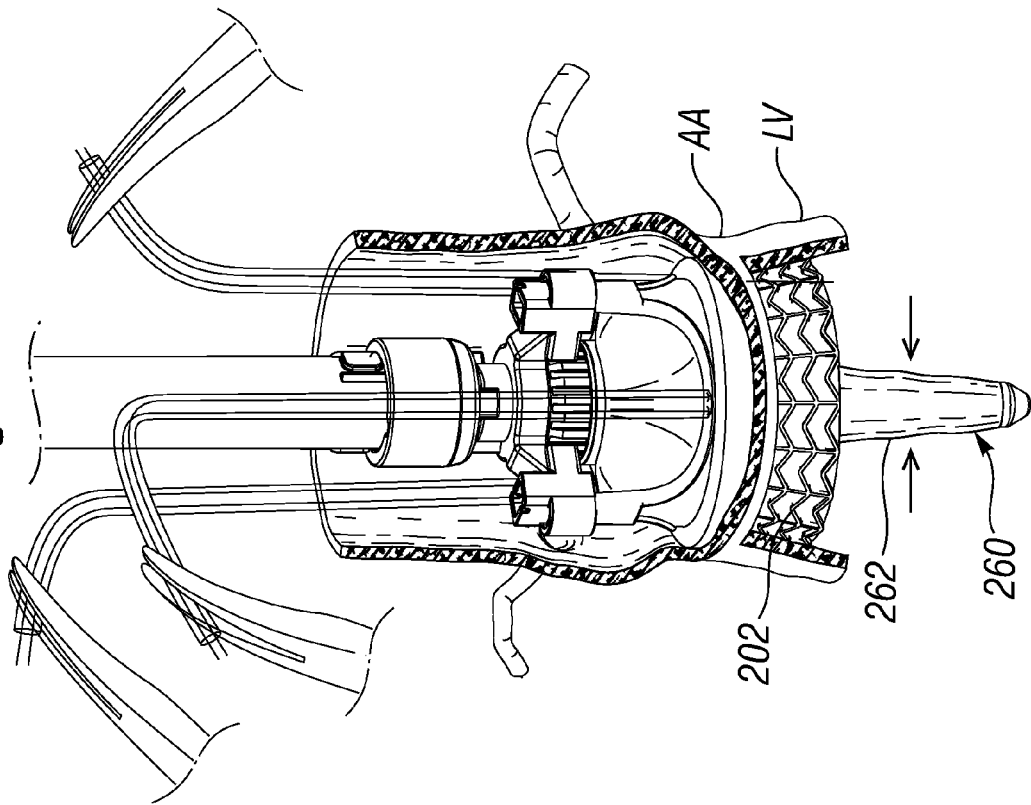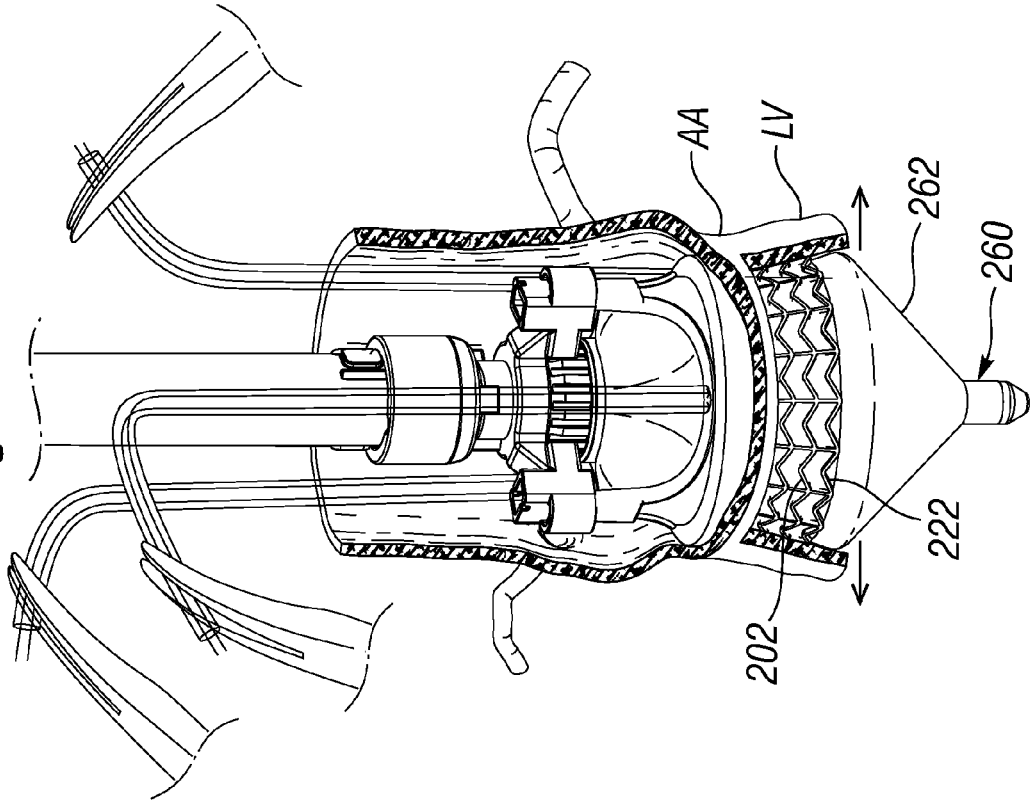

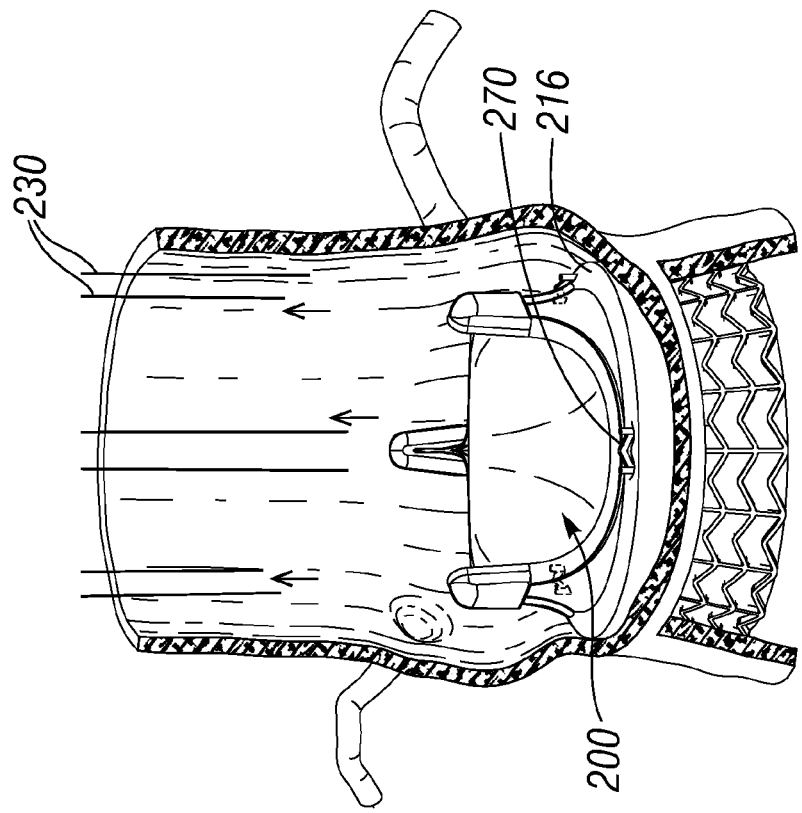
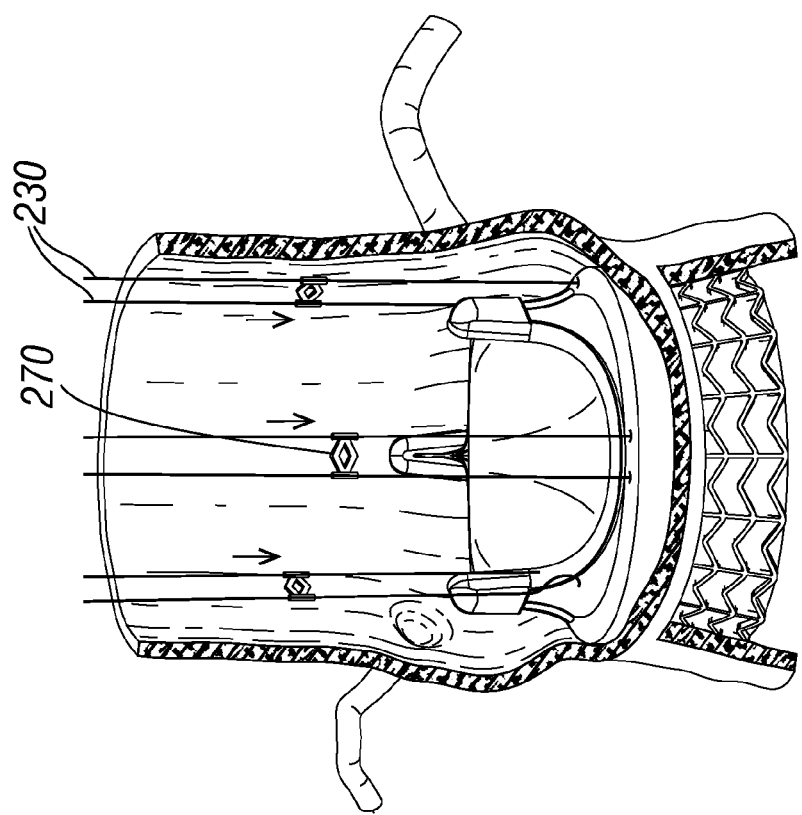

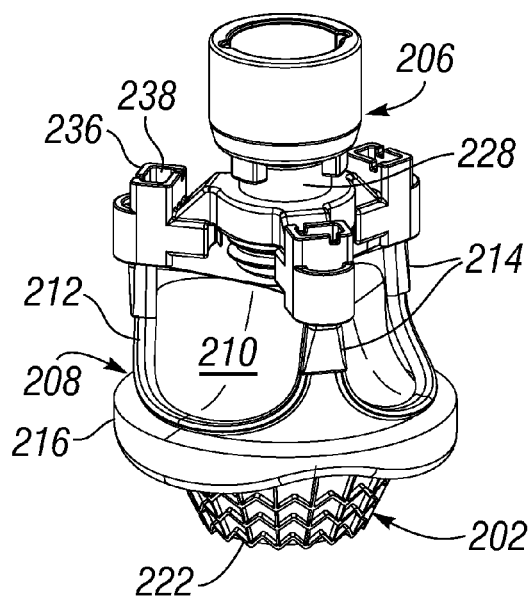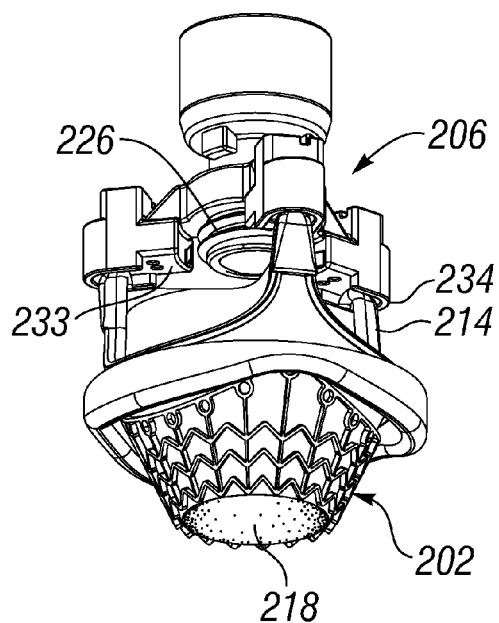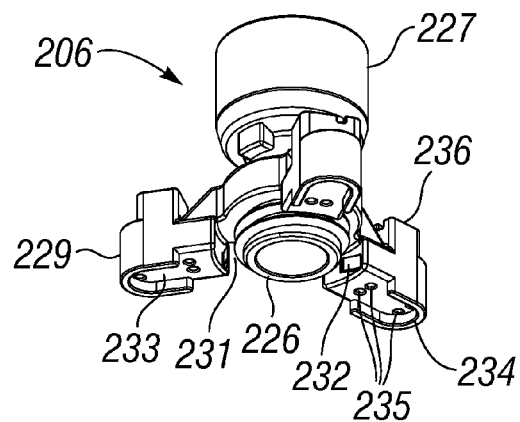

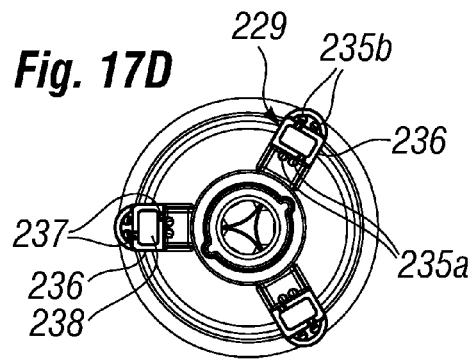
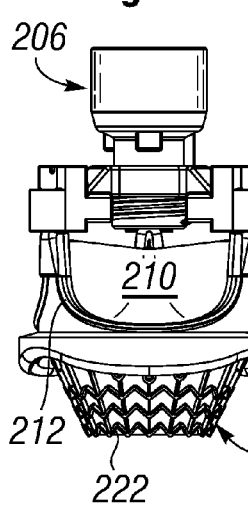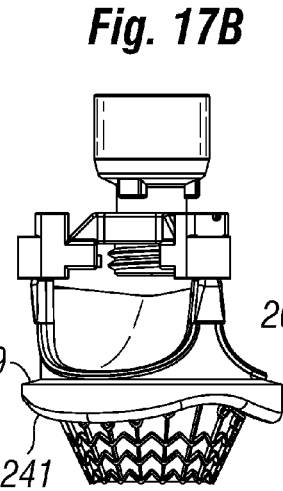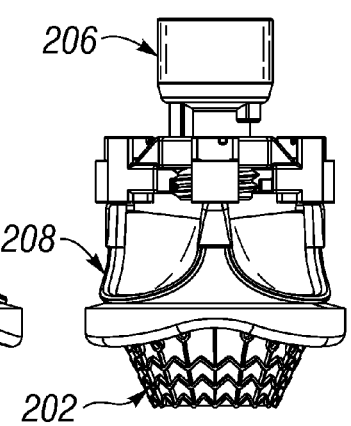
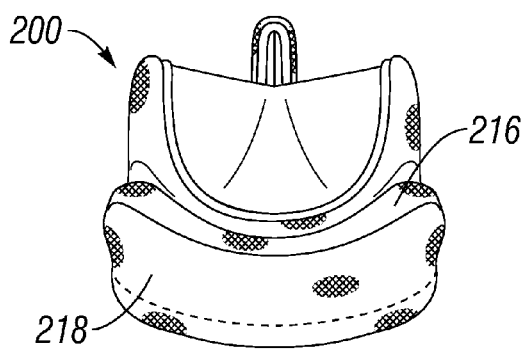

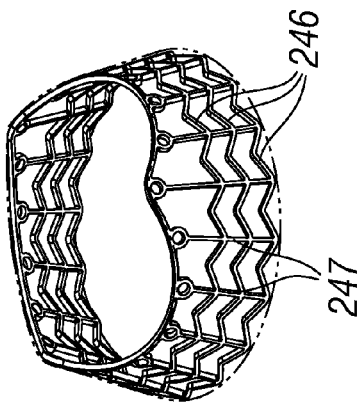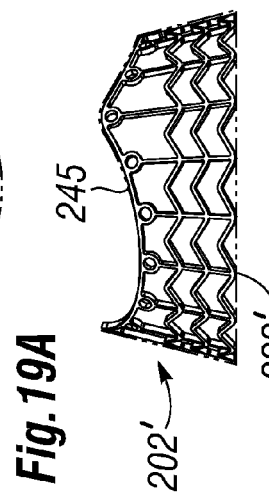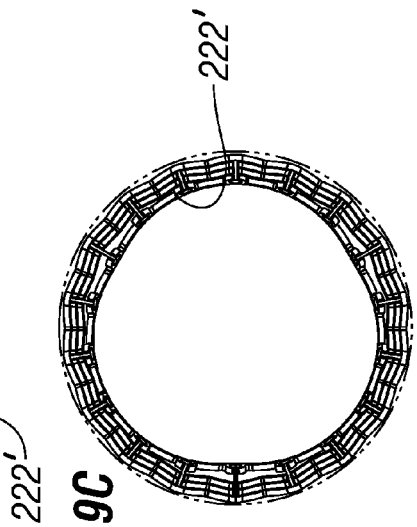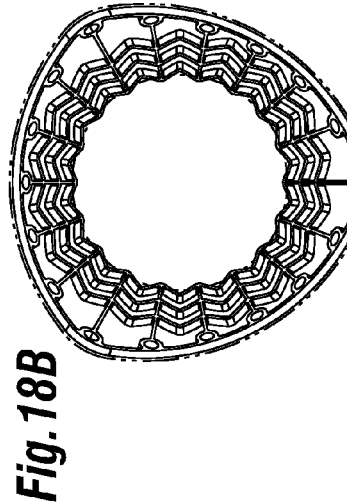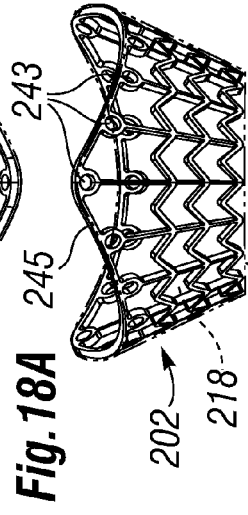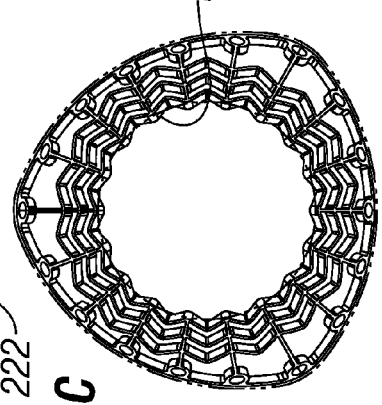

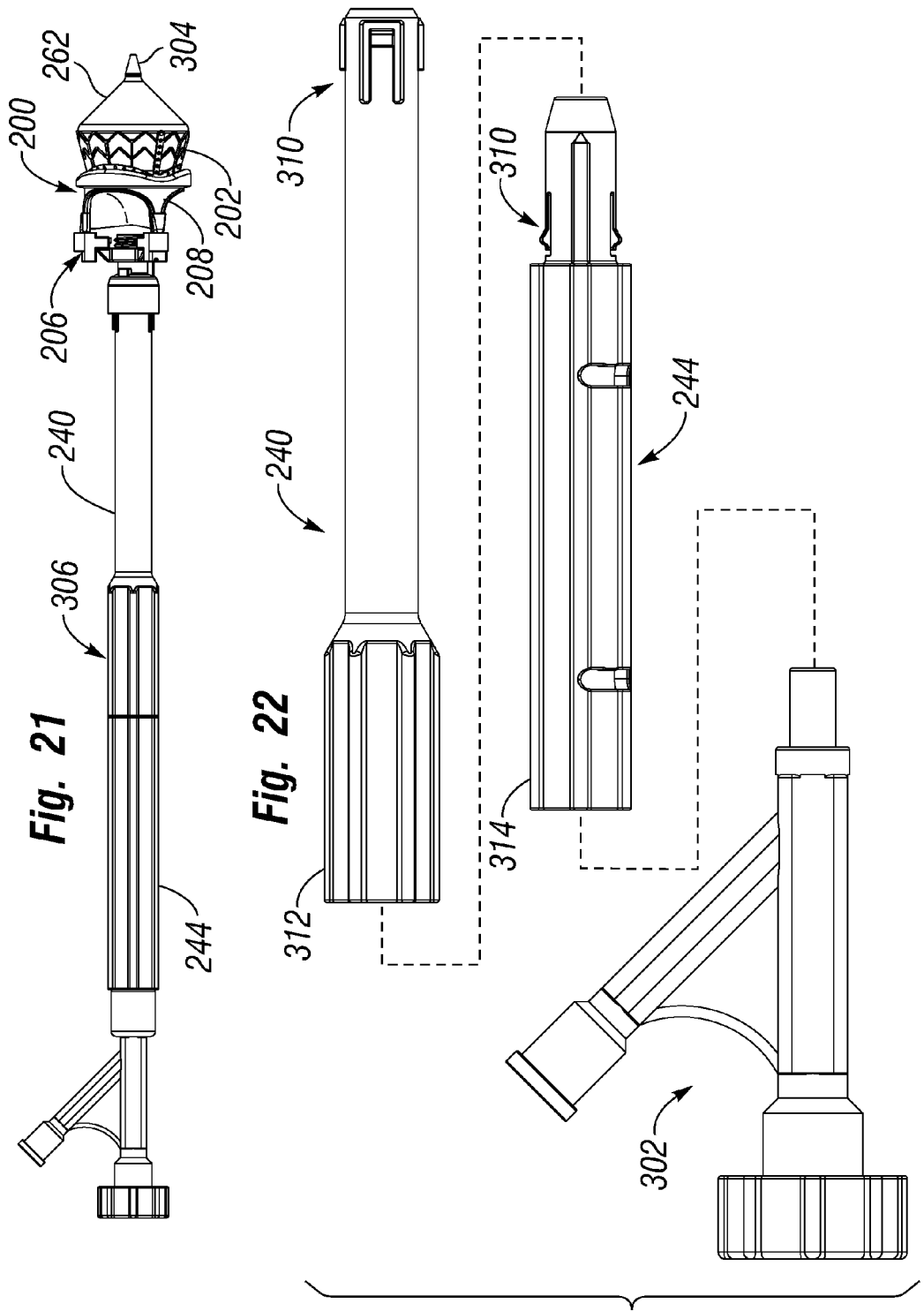

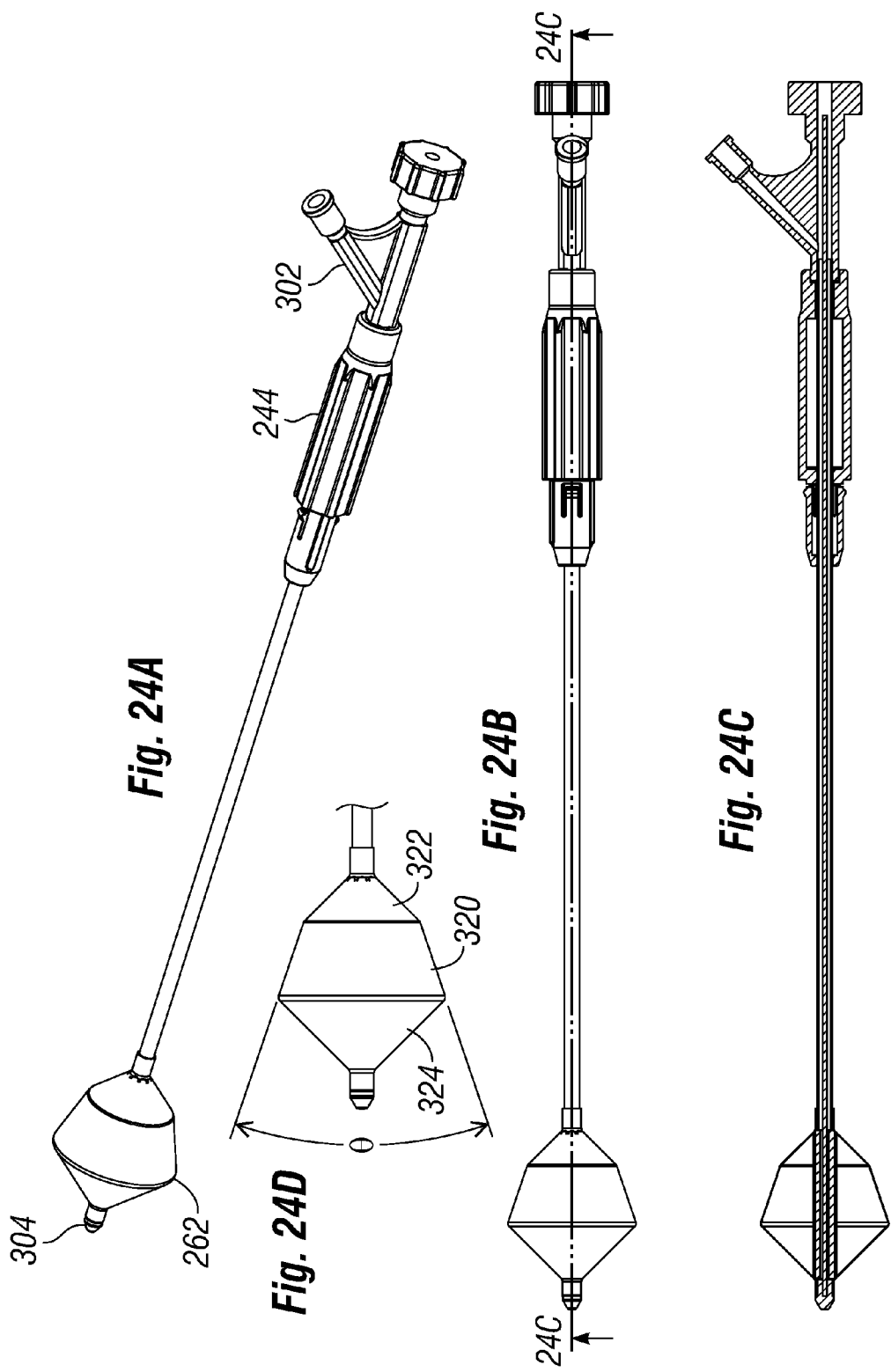

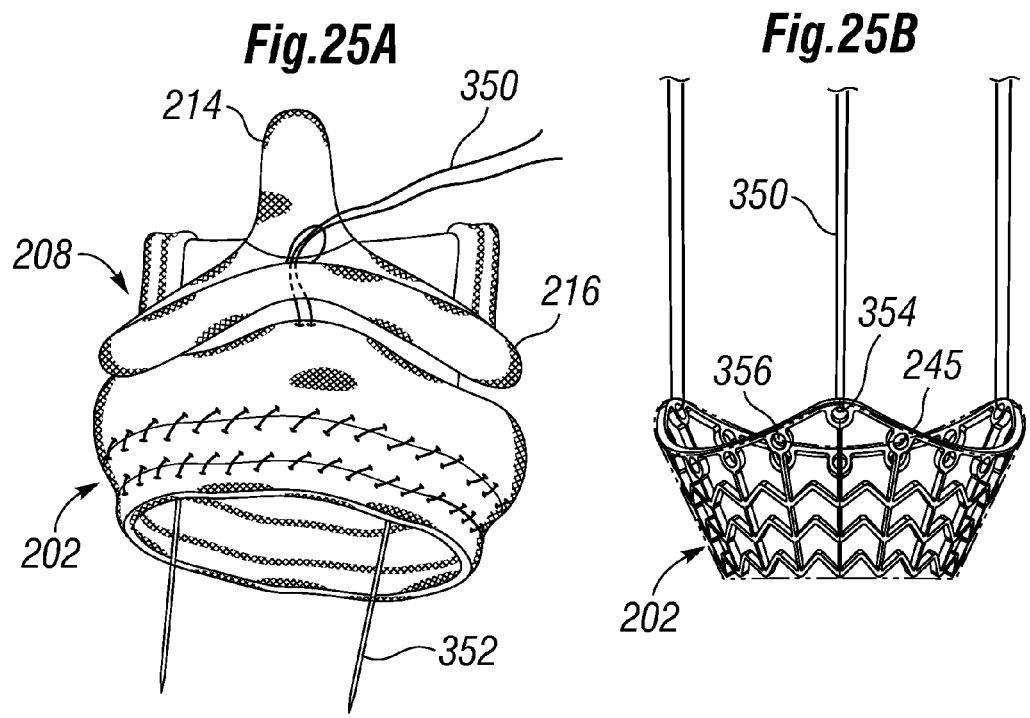
Fig.25A
Fig.25B
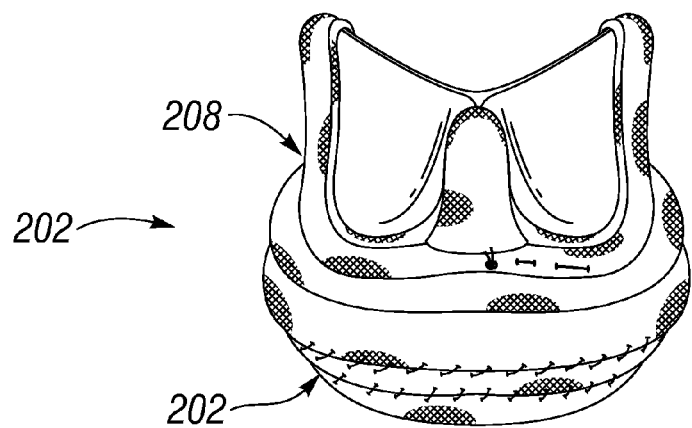
Fig.25C

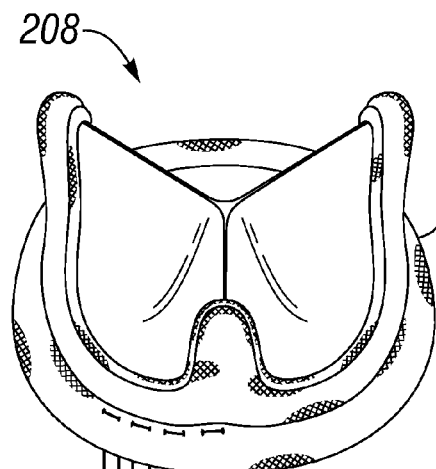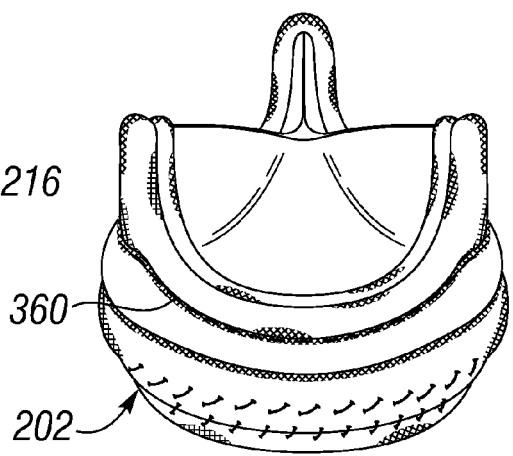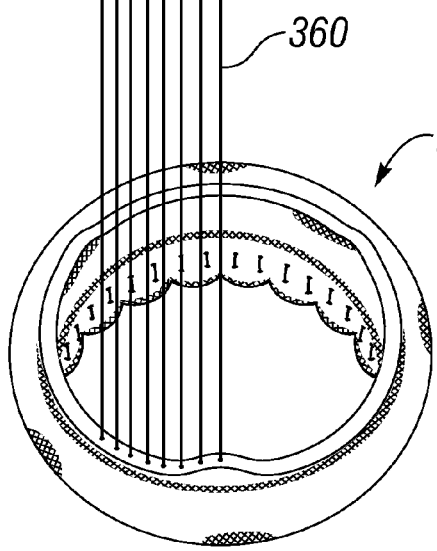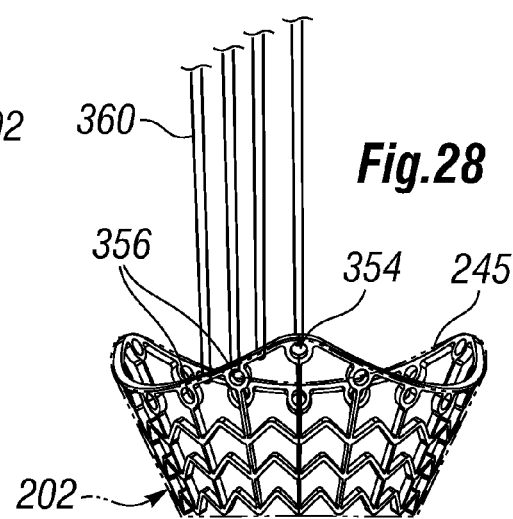

UNITARY QUICK CONNECT PROSTHETIC HEART VALVE AND DEPLOYMENT SYSTEM AND METHODS

RELATED APPLICATION

This application claims priority to U.S. Provisional Application No. 61/220,968, filed Jun. 26, 2009, the entire disclosure of which is incorporated by reference herewith.

FIELD OF THE INVENTION

The present invention generally relates to prosthetic valves for implantation in body channels. More particularly, the present invention relates to unitary prosthetic heart valves configured to be surgically implanted in less time than current valves.

BACKGROUND OF THE INVENTION

In vertebrate animals, the heart is a hollow muscular organ having four pumping chambers as seen in FIG. 1—the left and right atria and the left and right ventricles, each provided with its own one-way valve. The natural heart valves are identified as the aortic, mitral (or bicuspid), tricuspid and pulmonary, and are each mounted in an annulus comprising dense fibrous rings attached either directly or indirectly to the atrial and ventricular muscle fibers. Each annulus defines a flow orifice.

The atria are the blood-receiving chambers, which pump blood into the ventricles. The ventricles are the blood-discharging chambers. A wall composed of fibrous and muscular parts, called the interatrial septum separates the right and left atria (see FIGS. 2 to 4). The fibrous interatrial septum is a materially stronger tissue structure compared to the more friable muscle tissue of the heart. An anatomic landmark on the interatrial septum is an oval, thumbprint sized depression called the oval fossa, or fossa ovalis (shown in FIG. 4).

The synchronous pumping actions of the left and right sides of the heart constitute the cardiac cycle. The cycle begins with a period of ventricular relaxation, called ventricular diastole. The cycle ends with a period of ventricular contraction, called ventricular systole. The four valves (see FIGS. 2 and 3) ensure that blood does not flow in the wrong direction during the cardiac cycle; that is, to ensure that the blood does not back flow from the ventricles into the corresponding atria, or back flow from the arteries into the corresponding ventricles. The mitral valve is between the left atrium and the left ventricle, the tricuspid valve between the right atrium and the right ventricle, the pulmonary valve is at the opening of the pulmonary artery, and the aortic valve is at the opening of the aorta.

FIGS. 2 and 3 show the anterior (A) portion of the mitral valve annulus abutting the non-coronary leaflet of the aortic valve. The mitral valve annulus is in the vicinity of the circumflex branch of the left coronary artery, and the posterior (P) side is near the coronary sinus and its tributaries.

The mitral and tricuspid valves are defined by fibrous rings of collagen, each called an annulus, which forms a part of the fibrous skeleton of the heart. The annulus provides peripheral attachments for the two cusps or leaflets of the mitral valve (called the anterior and posterior cusps) and the three cusps or leaflets of the tricuspid valve. The free edges of the leaflets connect to chordae tendineae from more than one papillary muscle, as seen in FIG. 1. In a healthy heart, these muscles and their tendinous chords support the mitral and tricuspid valves, allowing the leaflets to resist the high pressure developed during contractions (pumping) of the left and right ventricles.

When the left ventricle contracts after filling with blood from the left atrium, the walls of the ventricle move inward and release some of the tension from the papillary muscle and chords. The blood pushed up against the under-surface of the mitral leaflets causes them to rise toward the annulus plane of the mitral valve. As they progress toward the annulus, the leading edges of the anterior and posterior leaflet come together forming a seal and closing the valve. In the healthy heart, leaflet coaptation occurs near the plane of the mitral annulus. The blood continues to be pressurized in the left ventricle until it is ejected into the aorta. Contraction of the papillary muscles is simultaneous with the contraction of the ventricle and serves to keep healthy valve leaflets tightly shut at peak contraction pressures exerted by the ventricle.

Various surgical techniques may be used to repair a diseased or damaged valve. In a valve replacement operation, the damaged leaflets are excised and the annulus sculpted to receive a replacement valve. Due to aortic stenosis and other heart valve diseases, thousands of patients undergo surgery each year wherein the defective native heart valve is replaced by a prosthetic valve, either bioprosthetic or mechanical. Another less drastic method for treating defective valves is through repair or reconstruction, which is typically used on minimally calcified valves. The problem with surgical therapy is the significant insult it imposes on these chronically ill patients with high morbidity and mortality rates associated with surgical repair.

When the valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective valves are deemed inoperable because their condition is too frail to withstand the procedure. By some estimates, about 30 to 50% of the subjects suffering from aortic stenosis who are older than 80 years cannot be operated on for aortic valve replacement.

Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For instance, U.S. Pat. No. 5,411,552 to Andersen et al. describes a collapsible valve percutaneously introduced in a compressed state through a catheter and expanded in the desired position by balloon inflation. Although these remote implantation techniques have shown great promise for treating certain patients, replacing a valve via surgical intervention is still the preferred treatment procedure. One hurdle to the acceptance of remote implantation is resistance from doctors who are understandably anxious about converting from an effective, if imperfect, regimen to a novel approach that promises great outcomes but is relatively foreign. In conjunction with the understandable caution exercised by surgeons in switching to new techniques of heart valve replacement, regulatory bodies around the world are moving slowly as well. Numerous successful clinical trials and follow-up studies are in process, but much more experience with these new technologies will be required before they are completely accepted.

Accordingly, there is a need for an improved device and associated method of use wherein a prosthetic valve can be surgically implanted in a body channel in a more efficient procedure that reduces the time required on extracorporeal circulation. It is desirable that such a device and method be capable of helping patients with defective valves that are deemed inoperable because their condition is too frail to withstand a lengthy conventional surgical procedure.

Furthermore, surgeons relate that one of the most difficult tasks when attempting minimally invasive heart valve implantation or implantation through a small incision is tying the suture knots that hold the valve in position. A typical aortic valve implant utilizes 12-24 sutures (commonly 15) distributed evenly around and manually tied on one side of the sewing ring. The knots directly behind the commissure posts are particularly challenging because of space constraints. Eliminating the need to tie suture knots or even reducing the number of knots to those that are more accessible would greatly facilitate the use of smaller incisions that reduces infection risk, reduces the need for blood transfusions and allows more rapid recovery compared to patients whose valves are implanted through the full sternotomy commonly used for heart valve implantation.

The present invention addresses these needs and others.

SUMMARY OF THE INVENTION

Various embodiments of the present application provide prosthetic valves and methods of use for replacing a defective native valve in a human heart. Certain embodiments are particularly well adapted for use in a surgical procedure for quickly and easily replacing a heart valve while minimizing time using extracorporeal circulation (i.e., bypass pump).

In one embodiment, a method for treating a native aortic valve in a human heart to replaces the function of the aortic valve, comprises: 1) accessing a native valve through an opening in a chest; 2) placing guiding sutures in the annulus 3) advancing a heart valve within a lumen of the annulus; and 4) plastically expanding a metallic coupling stent on the heart valve to mechanically couple to the annulus in a quick and efficient manner.

The native valve leaflets may be removed before delivering the prosthetic valve. Alternatively, the native leaflets may be left in place to reduce surgery time and to provide a stable base for fixing the coupling stent within the native valve. In one advantage of this method, the native leaflets recoil inward to enhance the fixation of the metallic coupling stent in the body channel. When the native leaflets are left in place, a balloon or other expansion member may be used to push the valve leaflets out of the way and thereby dilate the native valve before implantation of the coupling stent. The native annulus may be dilated between 1.0-5 mm from their initial orifice size to accommodate a larger sized prosthetic valve.

In accordance with a preferred aspect, a heart valve includes a prosthetic valve defining therein a non-expandable, non-collapsible orifice, and an expandable coupling stent extending from an inflow end thereof. The coupling stent has a contracted state for delivery to an implant position and an expanded state configured for outward connection to the base stent. Desirably, the coupling stent is plastically expandable.

In another aspect, a prosthetic heart valve for implant at a heart valve annulus, comprises:
a. a non-expandable, non-collapsible annular support structure defining a flow orifice, the support structure including a plurality of commissure posts projecting in an outflow direction;
b. flexible leaflets attached to the support structure and commissure posts and mounted to alternately open and close across the flow orifice;
c. a suture-permeable ring circumscribing an inflow end of the support structure; and
d. a plastically-expandable coupling stent having a first end extending around and connected at the inflow end of the support structure, the coupling stent having a second end projecting in the inflow direction away from the valve support structure and being capable of assuming a contracted state for delivery to an implant position and an expanded state wider than the first end for outward contact with an annulus.

In one embodiment, the heart valve comprises a commercially available prosthetic valve having a sewing ring, and the coupling stent attaches to the sewing ring. The contracted state of the coupling stent may be conical, tapering down in a distal direction. The coupling stent preferably comprises a plurality of radially expandable struts at least some of which are arranged in rows, wherein the distalmost row has the greatest capacity for expansion from the contracted state to the expanded state.

A method of delivery and implant of a prosthetic heart valve system is also disclosed herein, comprising the steps of:
providing a heart valve including a prosthetic valve having a non-expandable, non-collapsible orifice, the heart valve further including an expandable coupling stent extending from an inflow end thereof, the coupling stent having a contracted state for delivery to an implant position and an expanded state configured for outward connection to the annulus;
advancing the heart valve with the coupling stent in its contracted state to an implant position adjacent the annulus; and
plastically expanding the coupling stent to the expanded state in contact with and connected to the annulus.

One embodiment of the method further includes mounting the heart valve on a holder having a proximal hub and lumen therethrough. The holder mounts on the distal end of a handle having a lumen therethrough, and the method including passing a balloon catheter through the lumen of the handle and the holder and within the heart valve, and inflating a balloon on the balloon catheter to expand the coupling stent. The heart valve mounted on the holder may be packaged separately from the handle and the balloon catheter. Desirably, the contracted state of the coupling stent is conical, and the balloon on the balloon catheter has a larger distal expanded end than its proximal expanded end so as to apply greater expansion deflection to the coupling stent than to the prosthetic valve.

In the method where the coupling stent is conical, the coupling stent may comprise a plurality of radially expandable struts at least some of which are arranged in rows, wherein the row farthest from the prosthetic valve has the greatest capacity for expansion from the contracted state to the expanded state.

The method may employ a coupling stent with a plurality of radially expandable struts, wherein a row farthest from the prosthetic valve has alternating peaks and valleys. The distal end of the coupling stent thus expands more than the rest of the coupling stent so that the peaks in the row farthest from the prosthetic valve project outward into apertures in the base stent.

Another aspect described herein is a system for delivering a heart valve including a prosthetic valve having a non-expandable, non-collapsible orifice, and an expandable coupling stent extending from an inflow end thereof, the coupling stent having a contracted state for delivery to an implant position and an expanded state. The delivery system includes a valve holder connected to a proximal end of the heart valve, a balloon catheter having a balloon, and a handle configured to attach to a proximal end of the valve holder and having a lumen for passage of the catheter, wherein the balloon extends distally through the handle, past the holder and through the heart valve. In the system, the prosthetic valve is preferably a commercially available valve having a sewing ring to which the coupling stent attaches.

The contracted state of the coupling stent in the delivery system may be conical, tapering down in a distal direction. Furthermore, the balloon catheter further may include a generally conical nose cone on a distal end thereof that extends through the heart valve and engages a distal end of the coupling stent in its contracted state. Desirably, the handle comprises a proximal section and a distal section that may be coupled together in series to form a continuous lumen, wherein the distal section is adapted to couple to the hub of the holder to enable manual manipulation of the heart valve using the distal section prior to connection with the proximal handle section. In one embodiment, the balloon catheter and proximal handle section are packaged together with the balloon within the proximal section lumen. Alternatively, the heart valve mounted on the holder is packaged separately from the handle and the balloon catheter.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The invention will now be explained and other advantages and features will appear with reference to the accompanying schematic drawings wherein:

FIGS. 5A-5E are sectional views through an isolated aortic annulus showing a portion of the adjacent left ventricle below the ascending aorta, and illustrating a number of steps in sutureless deployment of an exemplary unitary prosthetic heart valve disclosed herein, namely:

FIG. 5A shows a unitary prosthetic heart valve mounted on a balloon catheter advancing into position within the aortic annulus;

FIG. 5B shows the unitary prosthetic heart valve in a desired implant position at the aortic annulus, with the balloon catheter advanced farther to displace a nose cone out of engagement with a coupling stent;

FIG. 5C shows the balloon on the catheter inflated to expand and deploy the flared coupling stent against and below the aortic annulus;

FIG. 5D shows the deflated balloon on the catheter along with the nose cone being removed from within the heart valve; and FIG. 5E shows the fully implanted unitary prosthetic heart valve;

FIG. 6 is an exploded view of an exemplary system for delivering the unitary prosthetic heart valve;

FIG. 7 is an assembled view of the delivery system of FIG. 6 showing a nose cone extending over a distal end of a valve coupling stent;

FIG. 8 is a view like FIG. 7 but with a balloon catheter displaced distally to disengage the nose cone from the coupling stent;

FIGS. 9A and 9B are perspective views of an exemplary unitary prosthetic heart valve assembled on a valve holder;

FIG. 9C is a side elevational view of the assembly of FIGS. 9A and 9B;

FIGS. 9D and 9E are distal and proximal plan views of the assembly of FIGS. 9A and 9B;

FIG. 12A-12D are plan views of still further alternative coupling stents;

FIGS. 13A-13K are perspective cutaway views of an aortic annulus showing a portion of the adjacent left ventricle below the ascending aorta, and illustrating a number of steps in deployment of an alternative unitary prosthetic heart valve disclosed herein, namely:

FIG. 13A shows the heart valve after removal from a storage and shipping jar and during attachment of an internally threaded leaflet parting sleeve to a heart valve holder;

FIG. 13B shows a preliminary step in preparing an aortic annulus for receiving the heart valve including installation of guide sutures;

FIG. 13C shows the heart valve mounted on distal section of a delivery handle advancing into position within the aortic annulus along the guide sutures;

FIG. 13D shows the heart valve in a desired implant position at the aortic annulus, and during placement of suture snares;

FIG. 13E shows forceps bending upper ends of the suture snares outward to improve access to the heart valve and implant site;

FIG. 13F shows a balloon catheter descending toward the implant site prior to insertion through the delivery handle, holder and heart valve;

FIG. 13G shows the delivery handle proximal and distal sections mated and the distal end of the balloon catheter below a coupling stent of the heart valve prior to inflation of the balloon;

FIG. 13H shows the balloon of the balloon catheter inflation to expand the coupling stent;

FIG. 13I shows the balloon deflated;

FIG. 13J shows three fastener clips descending down the guide sutures after removal of the snares;

FIG. 13K shows the fully implanted unitary prosthetic heart valve with the fastener clips secured on the proximal face of a sewing ring during removal of the guide sutures;

FIGS. 14 and 15 are upper and lower perspective views of the alternative unitary prosthetic heart valve assembled on the valve holder;

FIG. 16 is a lower perspective view of the valve holder of FIG. 14;

FIGS. 17A-17F are a number of plan and elevational views of the alternative unitary prosthetic heart valve and holder assembly of FIGS. 14 and 15;

FIGS. 18A-18C are elevational and top and bottom plan views of the coupling stent of the heart valve of FIGS. 14-17 with a second end in a contracted state and forming a conical shape;

FIGS. 19A-19D are elevational, top and bottom plan, and perspective views of the coupling stent of the heart valve of FIGS. 14-17 with the second end in an expanded state and also forming a conical shape;

FIG. 21 is an elevational view of the delivery system of FIGS. 20A-20C with the coupling stent of the heart valve;

FIG. 22 is an exploded view of several components of the delivery system of FIG. 21, without the balloon catheter, heart valve and holder;

FIGS. 24A-24D are perspective, elevational and longitudinal sectional views of the balloon catheter and proximal handle section of the delivery system of FIGS. 20A-20C.

FIGS. 25A and 25B schematically show an exemplary configuration for attaching the prosthetic valve to the coupling stent with temporary sutures to form the unitary prosthetic heart valve of the present application;

FIGS. 26A-26D and 27-29 illustrate several initial steps in an exemplary installation of permanent sutures between the prosthetic valve and coupling stent.

DETAILED DESCRIPTION OF THE PREFERRED EMBODIMENTS

Figure 1:
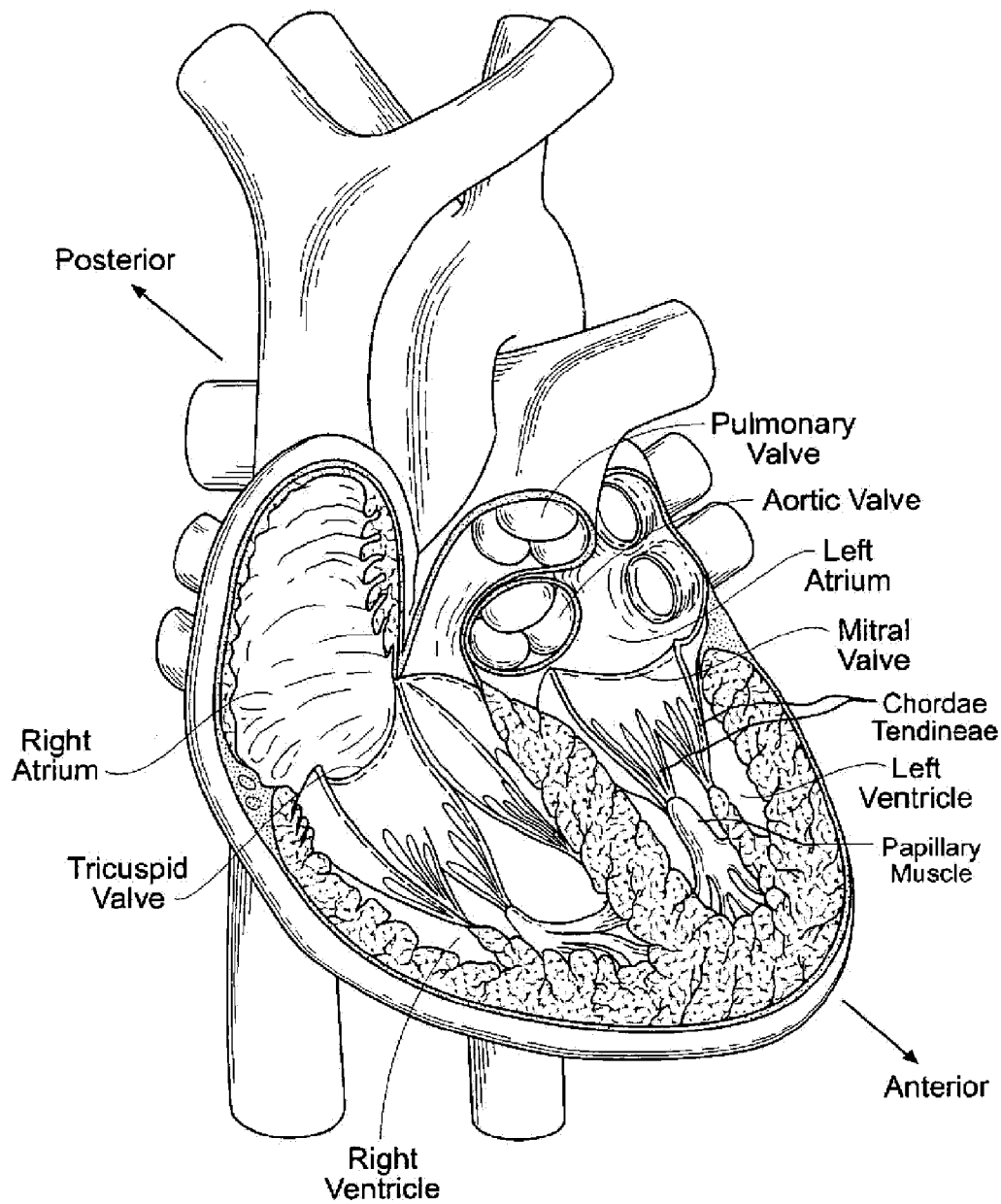
FIG. 1 is an anatomic anterior view of a human heart, with portions broken away and in section to view the interior heart chambers and adjacent structures.
Figure 2:
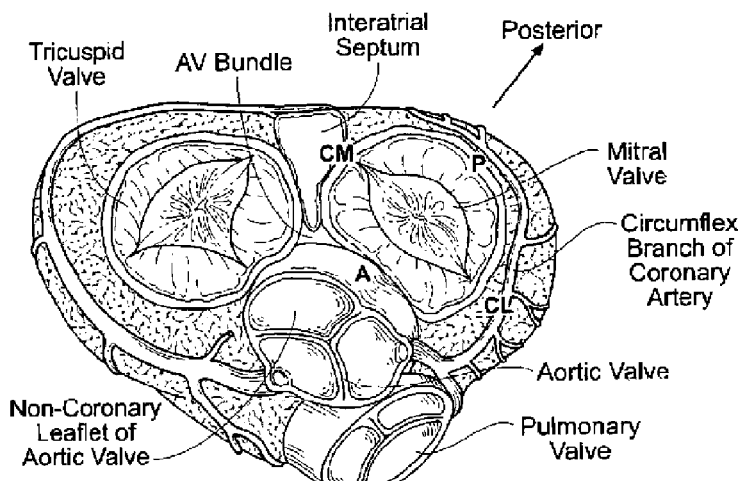
FIG. 2 is an anatomic superior view of a section of the human heart showing the tricuspid valve in the right atrium, the mitral valve in the left atrium, and the aortic valve in between, with the tricuspid and mitral valves open and the aortic and pulmonary valves closed during ventricular diastole (ventricular filling) of the cardiac cycle.
Figure 3:
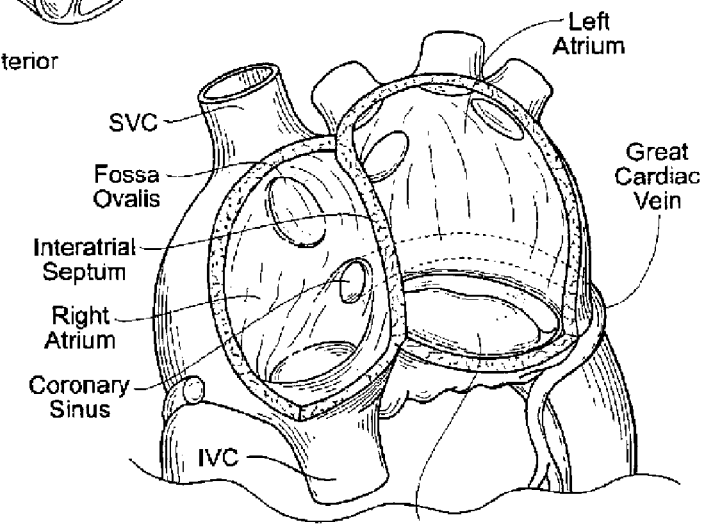
FIG. 3 is an anatomic superior view of a section of the human heart shown in FIG. 2, with the tricuspid and mitral valves closed and the aortic and pulmonary valves opened during ventricular systole (ventricular emptying) of the cardiac cycle.
Figure 4:
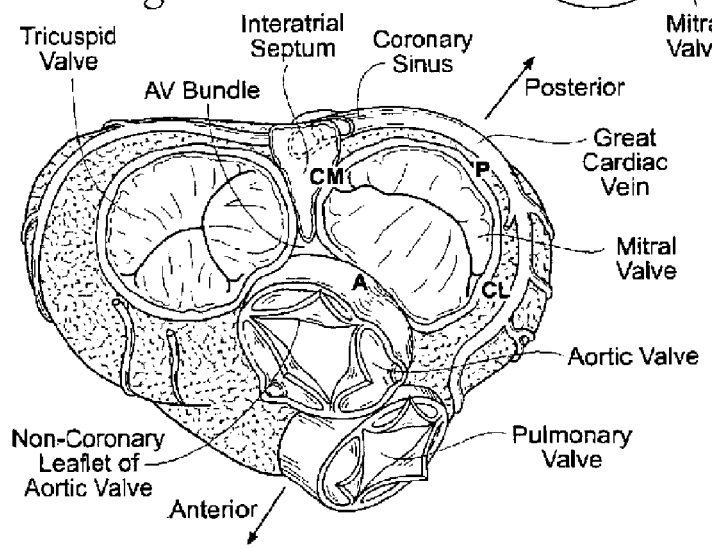
FIG. 4 is an anatomic anterior perspective view of the left and right atria, with portions broken away and in section to show the interior of the heart chambers and associated structures, such as the fossa ovalis, coronary sinus, and the great cardiac vein.

The present invention attempts to overcome drawbacks associated with conventional, open-heart surgery, while also adopting some of the techniques of newer technologies which decrease the duration of the treatment procedure. The prosthetic heart valves of the present invention are primarily intended to be delivered and implanted using conventional surgical techniques, including the aforementioned open-heart surgery. There are a number of approaches in such surgeries, all of which result in the formation of a direct access pathway to the particular heart valve annulus. For clarification, a direct access pathway is one that permits direct (i.e., naked eye) visualization of the heart valve annulus. In addition, it will be recognized that embodiments of the unitary prosthetic heart valves described herein may also be configured for delivery using percutaneous approaches, and those minimally-invasive surgical approaches that require remote implantation of the valve using indirect visualization.

One primary aspect of the present invention is a unitary prosthetic heart valve including implanting a tissue anchor at the same time as a valve member resulting in certain advantages. The exemplary unitary prosthetic heart valve of the present invention has a hybrid valve member with non-expandable and expandable portions. By utilizing an expandable stent coupled to a non-expandable valve member, the duration of the anchoring operation is greatly reduced as compared with a conventional sewing procedure utilizing an array of sutures. The expandable stent may simply be radially expanded outward into contact with the implantation site, or may be provided with additional anchoring means, such as barbs. The operation may be carried out using a conventional open-heart approach and cardiopulmonary bypass. In one advantageous feature, the time on bypass is greatly reduced due to the relative speed of implanting the expandable stent.

For definitional purposes, the terms "stent" or "coupling stent" refer to a structural component of a heart valve that is capable of attaching to tissue of a heart valve annulus. The coupling stents described herein are most typically tubular stents, or stents having varying shapes or diameters. A stent is normally formed of a biocompatible metal frame, such as stainless steel or Nitinol. More preferably, in the context of the present invention the stents are made from laser-cut tubing of a plastically-expandable metal. Other coupling stents that could be used with valves of the present invention include rigid rings, spirally-wound tubes, and other such tubes that fit tightly within a valve annulus and define an orifice therethrough for the passage of blood. It is entirely conceivable, however, that the coupling stent could be separate clamps or hooks that do not define a continuous periphery. Although such devices sacrifice some contact uniformity, and speed and ease of deployment, these devices could be configured to work in conjunction with a particular valve member.

A distinction between self-expanding and balloon-expanding stents exists in the field. A self-expanding stent may be crimped or otherwise compressed into a small tube and possesses sufficient elasticity to spring outward by itself when a restraint such as an outer sheath is removed. In contrast, a balloon-expanding stent is made of a material that is substantially less elastic, and indeed must be plastically expanded from the inside out when converting from a contracted to an expanded diameter. It should be understood that the term balloon-expanding stents encompasses plastically-expandable stents, whether or not a balloon is used to actually expand it (e.g., a device with mechanical fingers could expand the stent). The material of the stent plastically deforms after application of a deformation force such as an inflating balloon or expanding mechanical fingers. Consequently, the term "balloon-expandable stent" should be considered to refer to the material or type of the stent as opposed to the specific expansion means.

The term "valve member" refers to that component of a heart valve that possesses the fluid occluding surfaces to prevent blood flow in one direction while permitting it in another. As mentioned above, various constructions of valve members are available, including those with flexible leaflets and those with rigid leaflets, or even a ball and cage arrangement. The leaflets may be bioprosthetic, synthetic, metallic, or other suitable expedients.

A primary focus of the present invention is a unitary prosthetic heart valve having a single stage implantation in which a surgeon secures a hybrid coupling stent and valve member to a valve annulus as one unit or part. Certain features of the hybrid coupling stent and valve member are described in co-pending U.S. Provisional Application No. 61/139,398, filed Dec. 19, 2008, the contents of which are expressly incorporated herein. It should be noted that "two-stage" prosthetic valve delivery disclosed in the aforementioned application refers to the two primary steps of a) anchoring structure to the annulus, and then b) connecting a valve member, which does not necessarily limit the valve to just two parts. Likewise, the unitary valve described herein is especially beneficial in a single stage implant procedure, but that does not necessarily limit the overall system to just one part. For instance, the heart valve 30 disclosed herein could also use an expanding base stent which is then reinforced by the subsequently implanted heart valve. Because the heart valve 30 has a non-expandable and non-collapsible annular support structure, and a plastically-expandable coupling stent 36, it effectively resists recoil of a self-expanded base stent. That said, various claims appended hereto may exclude more than one part.

As a point of further definition, the term "expandable" is used herein to refer to a component of the heart valve capable of expanding from a first, delivery diameter to a second, implantation diameter. An expandable structure, therefore, does not mean one that might undergo slight expansion from a rise in temperature, or other such incidental cause such as fluid dynamics acting on leaflets or commissures. Conversely, "non-expandable" should not be interpreted to mean completely rigid or a dimensionally stable, as some slight expansion of conventional "non-expandable" heart valves, for example, may be observed.

In the description that follows, the term "body channel" is used to define a blood conduit or vessel within the body. Of course, the particular application of the prosthetic heart valve determines the body channel at issue. An aortic valve replacement, for example, would be implanted in, or adjacent to, the aortic annulus. Likewise, a mitral valve replacement will be implanted at the mitral annulus. Certain features of the present invention are particularly advantageous for one implantation site or the other, in particular the aortic annulus. However, unless the combination is structurally impossible, or excluded by claim language, any of the heart valve embodiments described herein could be implanted in any body channel.

A "quick-connect" aortic valve bio-prosthesis described herein is a surgically-implanted medical device for the treatment of aortic valve stenosis. The exemplary quick-connect device comprises an implantable bio-prosthesis and a delivery system for its deployment. The device, delivery system and method of use take advantage of the proven hemodynamic performance and durability of existing commercially available, non-expandable prosthetic heart valves, such as the Carpentier-Edwards PERIMOUNT Magna® Aortic Heart Valve available from Edwards Lifesciences of Irvine, Calif., while improving its ease of use and reducing total procedure time. This is mainly accomplished by eliminating the need to suture the bio-prosthesis onto the native annulus as is currently done per standard surgical practice, and typically requires 12-24 manually tied sutures around the valve perimeter. Also, the technique may obviate the need to excise the leaflets of the calcified valve and debride or smooth the valve annulus.

FIGS. 5A-5E are sectional views through an isolated aortic annulus AA showing a portion of the adjacent left ventricle LV and ascending aorta with sinus cavities S. The two coronary sinuses CS are also shown. The series of views show snapshots of a number of steps in deployment of an exemplary prosthetic heart valve system of the present invention, which comprises a unitary system. A coupling stent of a unitary prosthetic valve is deployed against the native leaflets or, if the leaflets are excised, against the debrided aortic annulus AA.

FIG. 5A shows a unitary heart valve 30 mounted on a balloon catheter 32 having a balloon 40 (FIG. 5B) in a deflated state near a distal end and advancing into position so that it is approximately axially centered at the aortic annulus AA. The unitary heart valve 30 comprises a prosthetic valve 34 and a coupling stent 36 attached to and projecting from a distal end thereof. In its radially constricted or undeployed state, the coupling stent 36 assumes a conical inward taper in the distal direction. The catheter 32 extends through the heart valve 30 and terminates in a distal nose cone 38 which has a conical or bell-shape and covers the tapered distal end of the coupling stent 36. As will be shown below, the catheter 32 extends through an introducing cannula and valve holder.

When used for aortic valve replacement, the prosthetic valve 34 preferably has three flexible leaflets which provide the fluid occluding surfaces to replace the function of the native valve leaflets. In various preferred embodiments, the valve leaflets may be taken from another human heart (cadaver), a cow (bovine), a pig (porcine valve) or a horse (equine). In other preferred variations, the valve member may comprise mechanical components rather than biological tissue. The three leaflets are supported by a non-expandable, non-collapsible annular support structure and a plurality of commissure posts projecting in an outflow direction. Typical prosthetic heart valves with flexible leaflets include a synthetic (metallic and/or polymeric) support structure of one or more components covered with cloth for ease of attachment of the leaflets.

For instance, in a preferred embodiment, the prosthetic valve 34 comprises a commercially available, non-expandable prosthetic heart valve, such as the Carpentier-Edwards PERIMOUNT Magna® Aortic Heart Valve available from Edwards Lifesciences. In this sense, a "commercially available" prosthetic heart valve is an off-the-shelf (i.e., suitable for stand-alone sale and use) prosthetic heart valve defining therein a non-expandable, non-collapsible support structure and having a sewing ring capable of being implanted using sutures through the sewing ring in an open-heart, surgical procedure. The particular approach into the heart used may differ, but in surgical procedures the heart is stopped and opened, in contrast to beating heart procedures where the heart remains functional. To reiterate, the terms "non-expandable" and "non-collapsible" should not be interpreted to mean completely rigid and dimensionally stable, merely that the valve is not expandable/collapsible like some proposed minimally-invasively or percutaneously-delivered valves.

The prosthetic valve 34 is provided with an expandable coupling mechanism in the form of the coupling stent 36 for securing the valve to the annulus. Although the coupling stent 36 is shown, the coupling mechanism may take a variety of different forms, but eliminates the need for connecting sutures and provides a rapid connection means as it does not require the time-consuming process of suturing it to the annulus.

An implant procedure involves delivering the heart valve 30 and expanding the coupling stent 36 at the aortic annulus. Because the valve 34 is non-expandable, the entire procedure is typically done using the conventional open-heart technique. However, because the coupling stent 36 is implanted by simple expansion, with reduced suturing, the entire operation takes less time. This hybrid approach will also be much more comfortable to surgeons familiar with the open-heart procedures and commercially available heart valves.

Moreover, the relatively small change in procedure coupled with the use of proven heart valves should create a much easier regulatory path than strictly expandable, remote procedures. Even if the system must be validated through clinical testing to satisfy the Pre-Market Approval (PMA) process with the FDA (as opposed to a 510k submission), at least the surgeon acceptance of the quick-connect heart valve 30 will be greatly streamlined with a commercial heart valve that is already proven, such as the Magna® Aortic Heart Valve.

Figure 5C:
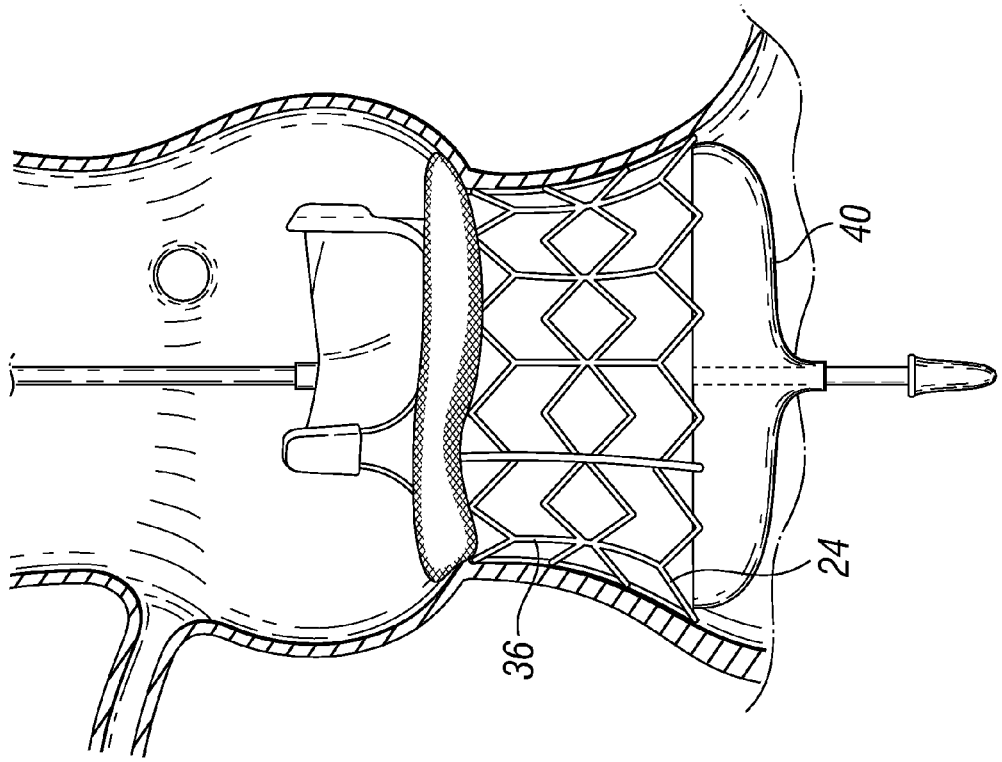
Figure 5B:
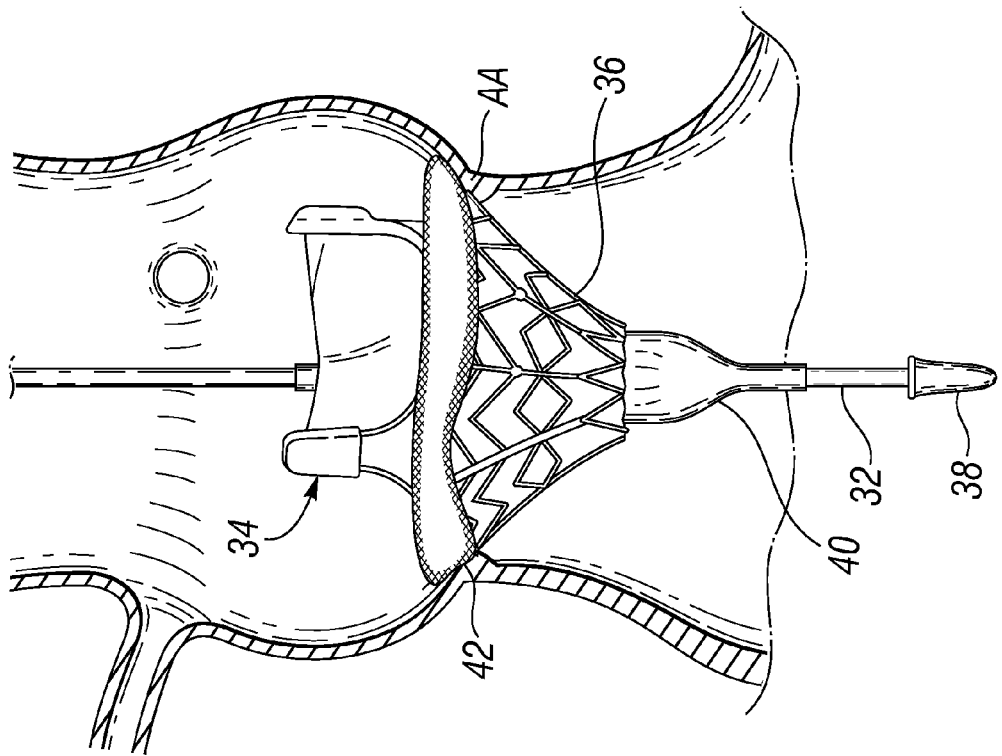

In FIG. 5B the heart valve 30 has advanced to a desired implant position at the aortic annulus AA. The prosthetic valve 34 may include a suture-permeable ring 42 that desirably abuts the aortic annulus AA. More preferably, the sewing ring 42 is positioned supra-annularly, or above the narrowest point of the aortic annulus AA, so as to allow selection of a larger orifice size than a valve placed intra-annularly. Furthermore, with annulus expansion using the coupling stent 36, and the supra-annular placement, the surgeon may select a valve having a size one or two increments larger than previously conceivable. As mentioned, the prosthetic valve 34 is desirably a commercially available heart valve having a sewing ring 42. The balloon catheter 32 has advanced relative to the heart valve 30 to displace the nose cone 38 out of engagement with the coupling stent 36. A dilatation balloon 40 on the catheter 32 can be seen just beyond the distal end of the coupling stent 36.

FIG. 5C shows the balloon 40 on the catheter 32 inflated to expand and deploy the coupling stent 36 against the annulus. The balloon 40 is desirably inflated using controlled, pressurized, sterile physiologic saline. The coupling stent 36 transitions between its conical contracted state and its generally tubular or slightly conical expanded state. Simple interference between the coupling stent 36 and the annulus may be sufficient to anchor the heart valve 30, or interacting features such as projections, hooks, barbs, fabric, etc. may be utilized.

In a preferred embodiment, the coupling stent 36 comprises a plastically-expandable cloth-covered stainless-steel tubular stent. One advantage of using a plastically-expandable stent is the ability to expand the native annulus to receive a larger valve size than would otherwise be possible with conventional surgery. Desirably, the left ventricular outflow tract (LVOT) is significantly expanded by at least 10%, or for example by 1.0-5 mm, and the surgeon can select a heart valve 30 with a larger orifice diameter relative to an unexpanded annulus. Even a 1 mm increase in annulus size is significant since the gradient is considered to be proportional to the radius raised to the $4^{th}$ power.

The stent body is preferably configured with sufficient radial strength for pushing aside the native leaflets and holding the native leaflets open in a dilated condition. The native leaflets provide a stable base for holding the stent, thereby helping to securely anchor the stent in the body. To further secure the stent to the surrounding tissue, the lower portion may be configured with anchoring members, such as, for example, hooks or barbs (not shown). It should be understood that the coupling stent 36 is desirably robust enough to anchor the heart valve 30 directly against the native annulus (with or without leaflet excision) in the absence of a pre-deployed base stent.

Also, the balloon 40 may have a larger distal expanded end than its proximal expanded end so as to apply more force to the free end of the coupling stent 36 than to the prosthetic valve 34. In this way, the prosthetic valve 34 and flexible leaflets therein are not subject to high expansion forces from the balloon 40. Indeed, although balloon deployment is shown, the coupling stent 36 may also be a self-expanding type of stent. In the latter configuration, the nose cone 38 is adapted to retain the coupling stent 36 in its constricted state prior to position in the heart valve 30 within the aortic annulus.

As noted above, the coupling stent 36 described herein can be a variety of designs, including having the diamond/chevron-shaped openings shown or other configurations. Further, the coupling stent 36 may include barbs or other tissue anchors to further secure the stent to the tissue. The barbs could be deployable (e.g., configured to extend or be pushed radially outward) by the expansion of a balloon. Alternatively, shape memory material may be utilized such that the barbs bend or curl upon implant. The material of the coupling stent 36 depends on the mode of delivery (i.e., balloon- or self-expanding), and the stent can be bare strut material or covered to promote ingrowth and/or to reduce paravalvular leakage. Preferably, the coupling stent 36 is covered to promote in-growth and/or to reduce paravalvular leakage, such as with a Dacron tube or the like.

Figure 5E:
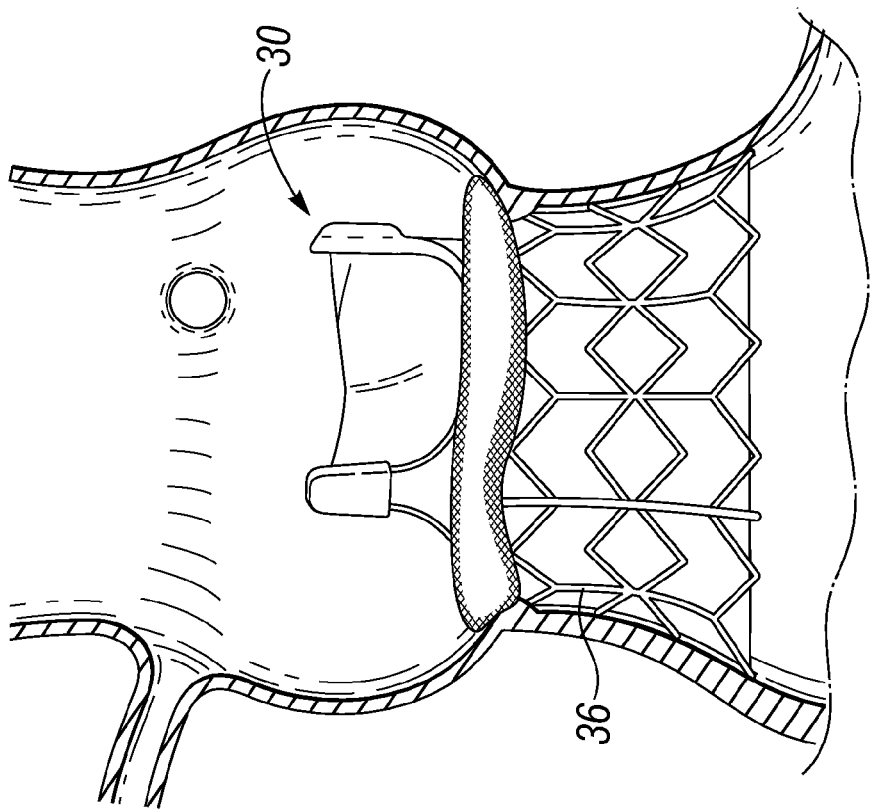
Figure 5D:
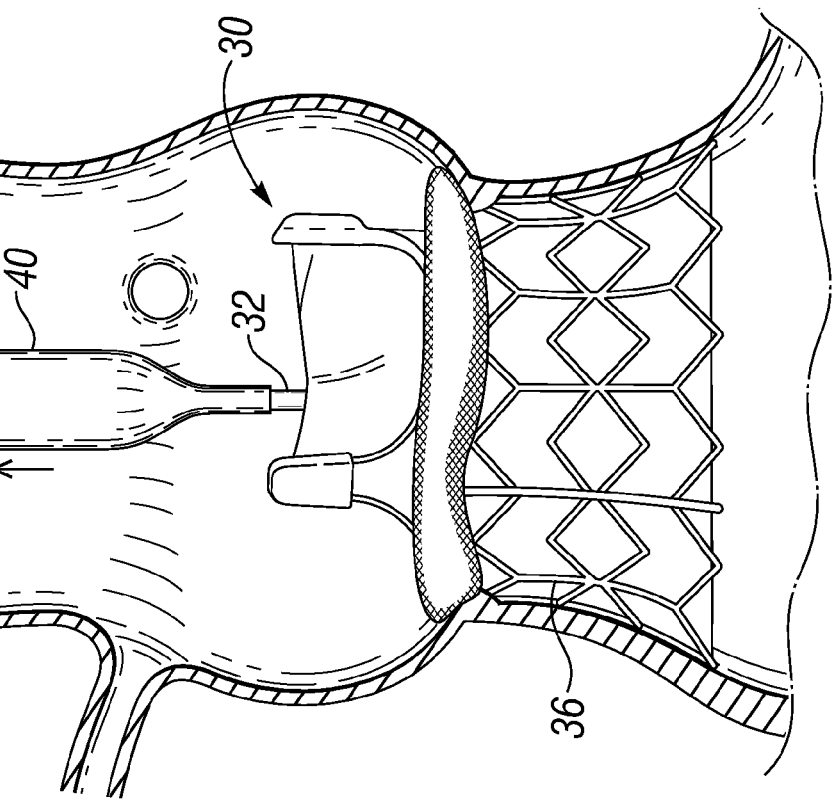

FIG. 5D shows the deflated balloon 40 on the catheter 32 along with the nose cone 38 being removed from within the heart valve 30. Finally, FIG. 5E shows the fully deployed prosthetic heart valve system of the present invention including the heart valve 30 coupled to the aortic annulus AA.

FIG. 6 is an exploded view, and FIGS. 7 and 8 are assembled views, of an exemplary system 50 for delivering the prosthetic heart valve of the present invention. The delivery system 50 includes a balloon catheter 52 having the balloon 40 on its distal end and an obturator 54 on a proximal end. The obturator 54 presents a proximal coupling 56 that receives a luer connector or other such fastener of a Y-fitting 58.

The aforementioned nose cone 38 may attach to the distal-most end of the catheter 52, but more preferably attaches to a wire (not shown) inserted through the center lumen of the balloon catheter 52. The nose cone 38 preferably secures to the end of a 0.035" guide wire and has a tapered geometry that fits onto the tapered geometry of the tapered coupling stent 36 to protect it and prevent accidental calcium dislodgement caused by the stent catching as it advances into the native calcified aortic valve. The nose cone 38 assembles onto the distal end of the heart valve 30 prior to positioning the device into the aortic root for deployment. The nose cone 38 is assembled by distally loading the guide wire into the through lumen of the balloon catheter 52 and advancing distally until it sits and conforms to the tapered coupling stent 36. Once the prosthesis is in the desired location and prior to balloon expansion, the surgeon advances the nose cone 38 in the ventricular direction to allow balloon expansion. As it advances in the ventricular direction and disengages the stent frame, the nose cone 38 collapses to a size that allows retrieval through the deployed aortic valve.

The catheter 52 and the nose cone 38 pass through a hollow handle 60 having a proximal section 62 and a distal section 64. A distal end of the distal handle section 64 firmly attaches to a hub 66 of a valve holder 68, which in turn attaches to the prosthetic heart valve 30. Details of the valve holder 68 will be given below with reference to FIGS. 9A-9E.

The two sections 62, 64 of the handle 60 are desirably formed of a rigid material, such as a molded plastic, and coupled to one another to form a relatively rigid and elongated tube for manipulating the prosthetic heart valve 30 attached to its distal end. In particular, the distal section 64 may be easily coupled to the holder hub 66 and therefore provide a convenient tool for managing the heart valve 30 during pre-surgical rinsing steps. For this purpose, the distal section 64 features a distal tubular segment 70 that couples to the holder hub 66, and an enlarged proximal segment 72 having an opening on its proximal end that receives a tubular extension 74 of the proximal handle section 62.

FIG. 6 shows an O-ring 76 that may be provided on the exterior of the tubular extension 74 for a frictional interference fit to prevent the two sections from disengaging. Although not shown, the distal tubular segment 70 may also have an O-ring for firmly coupling to the holder hub 66, or may be attached with threading or the like. In one preferred embodiment, the balloon 40 on the catheter 52 is packaged within the proximal handle section 62 for protection and ease of handling. Coupling the proximal and distal handle sections 62, 64 therefore "loads" the system 50 such that the balloon catheter 52 may be advanced through the continuous lumen leading to the heart valve 30.

In a preferred embodiment, the prosthetic heart valve 30 incorporates bioprosthetic tissue leaflets and is packaged and stored attached to the holder 68 but separate from the other introduction system 50 components. Typically, bioprosthetic tissue is packaged and stored in a jar with preservative solution for long shelf life, while the other components are packaged and stored dry.

When assembled as seen in FIGS. 7 and 8, an elongated lumen (not numbered) extends from the proximal end of the Y-fitting 58 to the interior of the balloon 40. The Y-fitting 58 desirably includes an internally threaded connector 80 for attachment to an insufflation system, or a side port 82 having a luer fitting 84 or similar expedient may be used for insufflation of the balloon 40.

FIGS. 7 and 8 show two longitudinal positions of the catheter 52 and associated structures relative to the handle 60 and its associated structures. In a retracted position shown in FIG. 7, the balloon 40 primarily resides within the distal handle section 64. FIG. 7 illustrates the delivery configuration of the introduction system 50, in which the surgeon advances the prosthetic heart valve 30 from outside the body into a location adjacent the target annulus. The nose cone 38 extends around and protects a distal end of the conical undeployed coupling stent 36. This configuration is also seen in FIG. 5A, albeit with the holder 68 removed for clarity. Note the spacing S between the proximal coupling 56 and the proximal end of the handle 60.

As explained above with respect to FIGS. 5A-5E, the surgeon advances the prosthetic heart valve 30 into its desired implantation position at the valve annulus, and then advances the balloon 40 through the heart valve and inflates it. To do so, the operator converts the delivery system 50 from the retracted configuration of FIG. 7 to the deployment configuration of FIG. 8, with the balloon catheter 40 displaced distally as indicated by the arrow 78 to disengage the nose cone 38 from the coupling stent 36. Note that the proximal coupling 56 now contacts the proximal end of the handle 60, eliminating the space S indicated in FIG. 7.

Prior to a further description of operation of the delivery system 50, a more detailed explanation of the heart valve 30 and valve holder 68 is necessary. FIGS. 9A-9E show a number of perspective and other views of the exemplary heart valve 30 mounted on the delivery holder 68 of the present invention. As mentioned, the heart valve 30 comprises the prosthetic valve 34 having the coupling stent 36 attached to an inflow end thereof. In a preferred embodiment, the prosthetic valve 34 comprises a commercially available off-the-shelf non-expandable, non-collapsible commercial prosthetic valve. Any number of prosthetic heart valves can be retrofit to attach the coupling stent 36, and thus be suitable for use in the context of the present invention. For example, the prosthetic valve 34 may be a mechanical valve or a valve with flexible leaflets, either synthetic or bioprosthetic. In a preferred embodiment, however, the prosthetic valve 34 includes bioprosthetic tissue leaflets 86 (FIG. 9A). Furthermore, as mentioned above, the prosthetic valve 34 is desirably a Carpentier-Edwards PERIMOUNT Magna® Aortic Heart Valve (e.g., model 3000TFX) available from Edwards Lifesciences of Irvine, Calif.

The coupling stent 36 preferably attaches to the ventricular (or inflow) aspect of the valve's sewing ring 42 during the manufacturing process in a way that preserves the integrity of the sewing ring and prevents reduction of the valve's effective orifice area (EOA). Desirably, the coupling stent 36 will be continuously sutured to the sewing ring 42 in a manner that maintains the outer contours of the sewing ring. Sutures may be passed through apertures or eyelets in the stent skeleton, or through a cloth covering that in turn is sewn to the skeleton. Other connection solutions include prongs or hooks extending inward from the stent, ties, Velcro, snaps, adhesives, etc. Alternatively, the coupling stent 36 may be more rigidly connected to rigid components within the prosthetic valve 34. During implant, therefore, the surgeon can seat the sewing ring 42 against the annulus in accordance with a conventional surgery. This gives the surgeon familiar tactile feedback to ensure that the proper patient-prosthesis match has been achieved. Moreover, placement of the sewing ring 42 against the outflow side of the annulus helps reduce the probability of migration of the heart valve 30 toward the ventricle.

The coupling stent 36 may be a pre-crimped, tapered, 316L stainless steel balloon-expandable stent, desirably covered by a polyester skirt 88 to help seal against paravalvular leakage and promote tissue ingrowth once implanted within the annulus (see FIG. 5E). The coupling stent 36 transitions between the tapered constricted shape of FIGS. 5A-5B and 9A-9E to its flared expanded shape shown in FIGS. 5C-5E.

The coupling stent 36 desirably comprises a plurality of sawtooth-shaped or otherwise angled, serpentine or web-like struts 90 connected to three generally axially-extending posts 92. As will be seen below, the posts 92 desirably feature a series of evenly spaced apertures to which sutures holding the polyester skirt 88 in place may be anchored. As seen best in FIG. 5E, the stent 36 when expanded flares outward and conforms closely against the inner surface of the annulus, and has an axial length as great as or greater than that of the prosthetic valve 34. Anchoring devices such as barbs or other protuberances from the coupling stent 36 may be provided to enhance the frictional hold between the coupling stent and the annulus.

It should be understood that the particular configuration of the coupling stent, whether possessing straight or curvilinear struts 90, may be modified as needed. There are numerous stent designs, as described below with reference to FIGS. 10-12D, any of which potentially may be suitable. Likewise, although the preferred embodiment incorporates a balloon-expandable coupling stent 36, a self-expanding stent could be substituted with certain modifications, primarily to the delivery system. In a preferred embodiment, the coupling stent 36 is desirably plastically-expandable to provide a firmer anchor for the valve 34 to the annulus with or without native leaflets. The stent may be expanded using a balloon or mechanical expander as described below.

Still with reference to FIGS. 9A-9E, the holder 68 comprises the aforementioned proximal hub 66 and a thinner distal extension 94 thereof forming a central portion of the holder. Three legs 96a, 96b, 96c circumferentially equidistantly spaced around the central extension 94 and projecting radially outward therefrom comprise inner struts 98 and outer commissure rests 100. The prosthetic valve 34 preferably includes a plurality, typically three, commissures 102 that project in an outflow direction. Although not shown, the commissure rests 100 preferably incorporate depressions into which the tips of the commissures 102 can fit.

In one embodiment, the holder 68 is formed of a rigid polymer such as Delrin or polypropylene that is transparent to increase visibility of an implant procedure. As best seen in FIG. 9E, the holder 68 exhibits openings between the legs 96a, 96b, 96c to provide a surgeon good visibility of the valve leaflets 86, and the transparency of the legs further facilitates visibility and permits transmission of light therethrough to minimize shadows. Although not described in detail herein, FIG. 9E also illustrate a series of through holes in the legs 96a, 96b, 96c permitting connecting sutures to be passed through fabric in the prosthetic valve 34 and across a cutting guide in each leg. As is known in the art, severing a middle length of suture that is connected to the holder 68 and passes through the valve permits the holder to be pulled free from the valve when desired.

FIGS. 9C and 9D illustrate a somewhat modified coupling stent 36 from that shown in FIGS. 9A and 9B, wherein the struts 90 and axially-extending posts 92 are better defined. Specifically, the posts 92 are somewhat wider and more robust than the struts 90, as the latter provide the stent 36 with the ability to expand from the conical shape shown to a more tubular configuration. Also, a generally circular reinforcing ring 104 abuts the valve sewing ring 42. Both the posts 92 and the ring 104 further include a series of through holes 106 that may be used to secure the polyester skirt 88 to the stent 36 using sutures or the like. A number of variants of the coupling stent 36 are also described below.

Figure 10A:
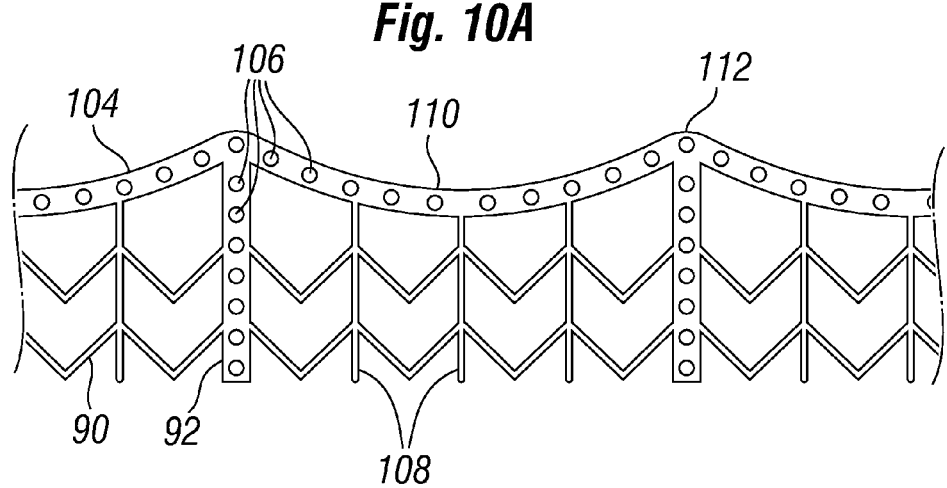
FIGS. 10A and 10B illustrate an exemplary coupling stent shown, respectively, in both a flat and a tubular expanded configuration.
Figure 10B:
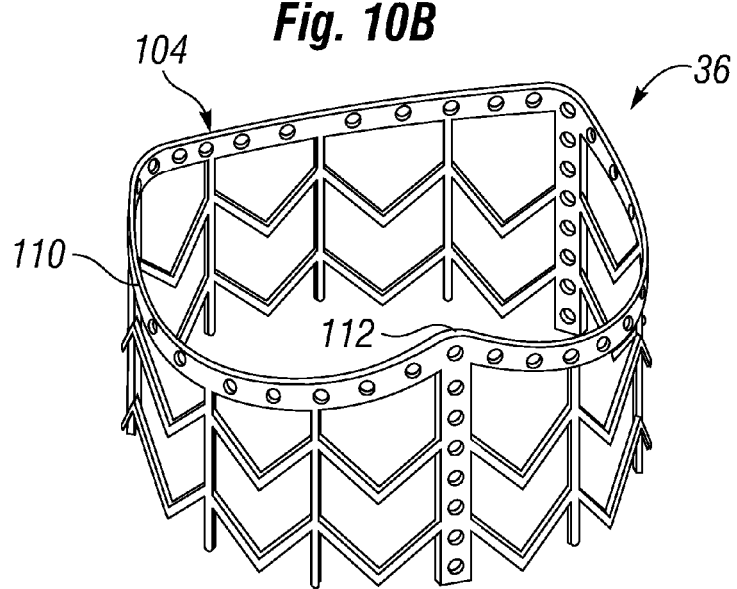

FIGS. 10A-10B illustrate the exemplary coupling stent 36 in both flat and tubular configurations, the latter which is generally the expanded shape. As mentioned, the web-like struts 90 and a reinforcing ring 104 connect three generally axially-extending posts 92. A plurality of evenly spaced apertures 106 provide anchors for holding the polyester skirt 88 (see FIG. 9B) in place. In the illustrated embodiment, the web-like struts 90 also include a series of axially-extending struts 108. An upper end of the coupling stent 36 that connects to the sewing ring of the valve and is defined by the reinforcing ring 104 follows an undulating path with alternating arcuate troughs 110 and peaks 112. As seen from FIG. 9C, the exemplary prosthetic valve 34 has an undulating sewing ring 42 to which the upper end of the coupling stent 36 conforms. In a preferred embodiment, the geometry of the stent 36 matches that of the undulating sewing ring 42. Of course, if the sewing ring of the prosthetic valve is planar, then the upper end of the coupling stent 36 will also be planar. It should be noted also that the tubular version of FIG. 10B is an illustration of an expanded configuration, although the balloon 40 may over-expand the free (lower) end of the stent 36 such that it ends up being slightly conical.

Figure 11A:
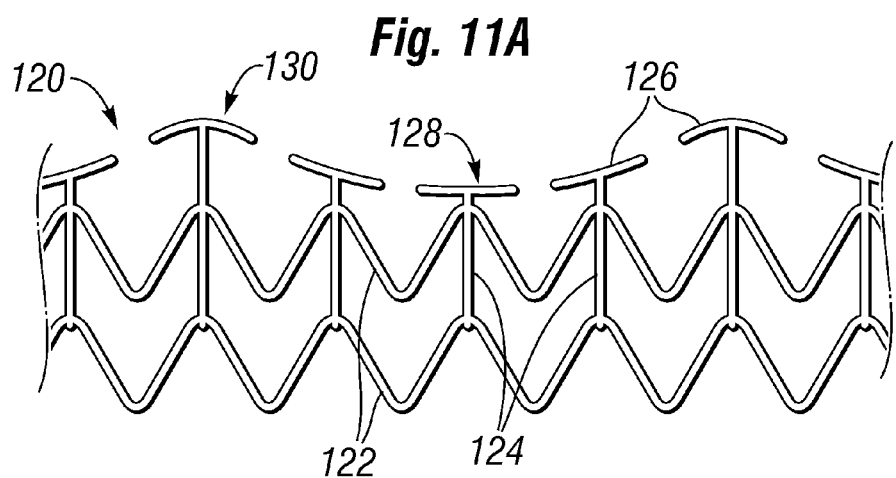
FIGS. 11A-11B illustrate an alternative coupling stent having a discontinuous upper end in both flat and tubular expanded configurations.
Figure 11B:
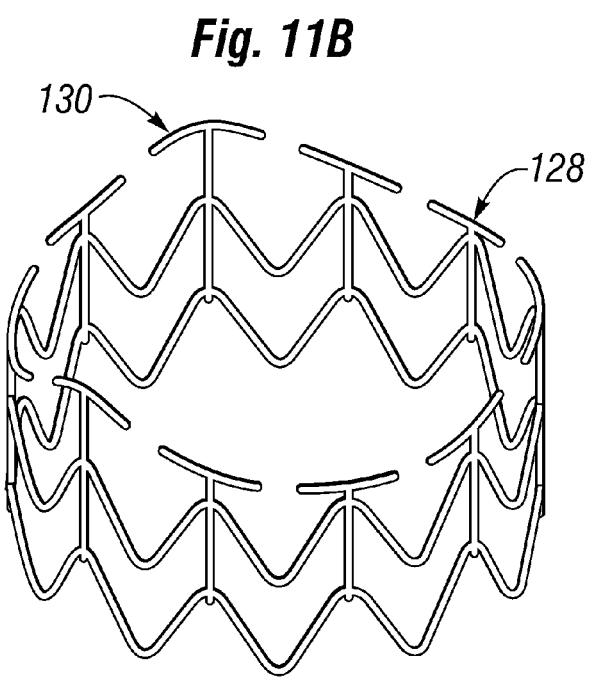

FIGS. 11A and 11B show an alternative coupling stent 120, again in flattened and tubular configurations, respectively. As with the first embodiment, the coupling stent 120 includes web-like struts 122 extending between a series of axially-extending struts 124. In this embodiment, all of the axially-extending struts 124 are substantially the same thin cross-sectional size. The upper or connected end of the stent 120 again includes a reinforcing ring 126, although this version is interrupted with a series of short lengths separated by gaps. The upper end defines a plurality of alternating troughs 128 and peaks 130, with lengths of the reinforcing ring 126 defining the peaks. The axially-extending struts 124 are in-phase with the scalloped shape of the upper end of the stent 120, and coincide with the peaks and the middle of the troughs.

The gaps between the lengths making up the reinforcing ring 126 permit the stent 120 to be matched with a number of different sized prosthetic valves 34. That is, the majority of the stent 120 is expandable having a variable diameter, and providing gaps in the reinforcing ring 126 allows the upper end to also have a variable diameter so that it can be shaped to match the size of the corresponding sewing ring. This reduces manufacturing costs as correspondingly sized stents need not be used for each different sized valve.

FIG. 12A is a plan view of a still further alternative coupling stent 132 that is very similar to the coupling stent 120, including web-like struts 134 connected between a series of axially-extending struts 136, and the upper end is defined by a reinforcing ring 138 formed by a series of short lengths of struts. In contrast to the embodiment of FIGS. 11A and 11B, the peaks of the undulating upper end have gaps as opposed to struts. Another way to express this is that the axially-extending struts 136 are out-of-phase with the scalloped shape of the upper end of the stent 132, and do not correspond to the peaks and the middle of the troughs.

FIG. 12B illustrates an exemplary coupling stent 140 again having the expandable struts 142 between the axially-extending struts 144, and an upper reinforcing ring 146. The axially-extending struts 144 are in-phase with peaks and troughs of the upper end of the stent. The reinforcing ring 146 is a cross between the earlier-described such rings as it is continuous around its periphery but also has a variable thickness or wire diameter. That is, the ring 146 comprises a series of lengths of struts 148 of fixed length connected by thinner bridge portions 150 of variable length, or in other words which are extendible. The bridge portions 150 are each formed with a radius so that they can be either straightened (lengthened) or bent more (compressed). A series of apertures 152 are also formed in an upper end of the stent 142 provide anchor points for sutures or other attachment means when securing the stent to the sewing ring of the corresponding prosthetic valve.

In FIG. 12C, an alternative coupling stent 154 is identical to the stent 140 of FIG. 12B, although the axially-extending struts 156 are out-of-phase with the peaks and troughs of the undulating upper end.

FIG. 12D shows a still further variation on a coupling stent 160, which has a series of expandable web-like struts 162 in sawtooth patterns connecting axially-extending struts 164. As with the version shown in FIGS. 10A and 10B, the web-like struts 162 are also connected by a series of axially-extending struts 166, although these are thinner than the main axial struts 164. A reinforcing ring 168 is also thicker than the web-like struts 162, and features one or more gaps 170 in each trough such that the ring is discontinuous and expandable. Barbs 172, 174 on the axially extending struts 164, 166 may be utilized to enhance retention between the coupling stent 160 and annular tissue within which it seats.

As an alternative to a balloon, a mechanical expander (not shown) may be used to expand the coupling stent 36 shown above. For instance, a mechanical expander may include a plurality of spreadable fingers actuated by a syringe-like apparatus, as seen in U.S. Provisional Application No. 61/139,398, incorporated above. The fingers are axially fixed but capable of pivoting or flexing with respect to a barrel. The distal end of a plunger has an outer diameter that is greater than the diameter circumscribed by the inner surfaces of the spreadable fingers, such that distal movement of the plunger with respect to the barrel gradually cams the fingers outward within the coupling stent. Therefore, the term "plastically-expandable" encompasses materials that can be substantially deformed by an applied force to assume a different shape. Some self-expanding stents may be deformed to a degree by an applied force beyond their maximum expanded dimension, but the primary cause of the shape change is elastic rebound as opposed to a plastic deformation.

The unitary heart valve 30 described above may be mounted on a balloon catheter advanced into implant position thereon, or the balloon catheter may be introduced after the valve has been delivered to the annulus. FIGS. 13A-13K illustrate an implant sequence wherein a surgeon first delivers an alternative unitary heart valve 200 to an aortic annulus and then introduces a balloon catheter to deploy a coupling stent 202. It should be understood that the same procedure may be carried out using the aforementioned heart valve 30, as well as any combination of valve and coupling stent disclosed herein.

Figure 13A:
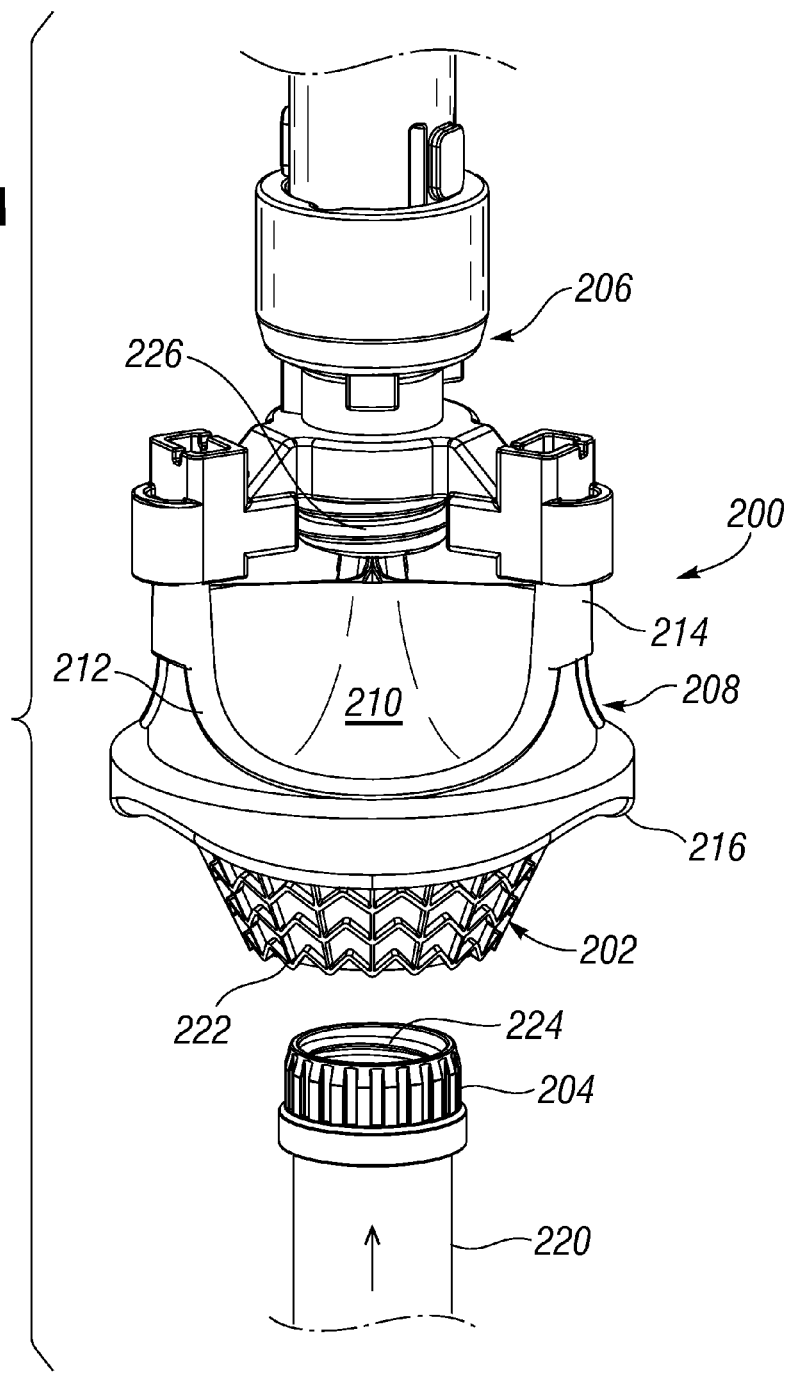

FIG. 13A shows the unitary heart valve 200 after removal from a storage and shipping jar and during attachment of an internally threaded leaflet parting sleeve 204 to a heart valve holder 206. The heart valve 200 is similar to the heart valve 30 described above in that it comprises a prosthetic valve 208 and the coupling stent 202 attached to and projecting from an inflow end thereof. The prosthetic valve 208 desirably has three flexible leaflets 210 supported by a non-expandable, non-collapsible annular support structure 212 and a plurality of commissure posts 214 projecting in an outflow direction. A suture-permeable ring 216 circumscribes an inflow end of the prosthetic valve 208. As mentioned above, the prosthetic valve 208 comprises a synthetic (metallic and/or polymeric) support structure of one or more components covered with cloth for ease of attachment of the leaflets. In one exemplary form, the prosthetic valve 208 is a commercially available, non-expandable prosthetic heart valve, such as the Carpentier-Edwards PERIMOUNT Magna® Aortic Heart Valve available from Edwards Lifesciences. Further details of the unitary heart valve 200 will be described below with reference to FIGS. 14-19.

In FIG. 13A and in the ensuing procedure drawings, the unitary heart valve 200 is oriented with an inflow end down and an outflow end up. Therefore, the terms inflow and down may be used interchangeably at times, as well as the terms outflow and up. Furthermore, the terms proximal and distal are defined from the perspective of the surgeon delivering the valve inflow end first, and thus proximal is synonymous with up or outflow, and distal with down or inflow.

The leaflet parting sleeve 204 mounts to one end of an assembly tube 220. Although not shown, the sleeve 204 preferably fits snugly over the end of the tube 220 with a slight interference, so that it may be decoupled therefrom with ease. Some form of minimal latch may also be provided. The coupling stent 202 has a first end (not shown) connected to the inflow end of the prosthetic valve 208 and a lower second end 222 that is shown in a contracted state for delivery to an implant position. In the contracted state, the coupling stent 202 assumes a frusto-conical shape wherein the lower second end 222 defines an opening large enough to receive the leaflet parting sleeve 204 with clearance therebetween. The sleeve 204 includes internal threading 224 that matches external threading on a downwardly-directed boss 226 of the valve holder 206. A technician passes the sleeve 204 on the end of the tube 220 through the stent second end 222, parts the flexible leaflets 210 from the inflow side, and screws the sleeve to the boss 226. Once the technician firmly attaches the sleeve 204, the assembly tube 220 may be easily pulled from and removed from within the valve 200. The resulting subassembly is seen in FIG. 13C.

Attachment of the leaflet parting sleeve 204 in this manner provides several benefits. First and foremost, the sleeve 204 defines a throughbore at the level of the valve leaflets 210 for passage of a balloon catheter from the outflow side. Typically three valve leaflets 210 span the orifice defined by the support structure 212 and have free edges that come together or "coapt" generally along three line segments oriented 120° apart that intersect at the centerline. This configuration mimics a native valve and performs well in permitting blood flow in one direction but not the other. Though extremely durable in use, the valve leaflets 210 are relatively fragile and susceptible to damage from contact with solid objects during the implant procedure, especially if they are made from bioprosthetic tissue such as bovine pericardium or a porcine xenograft. Consequently, the parting sleeve 204 opens the leaflets 210 and provides a protective barrier between them and a balloon catheter that passes through the valve, as will be seen below. Without the sleeve 204 a balloon catheter would have to force its way backward past the coapted leaflet free edges. A further benefit of the parting sleeve 204 is the ease with which it is assembled to the holder 206. Attachment through the valve 200 to the holder 206 is intuitive, and removal of the assembly sleeve 220 simple. The valve 220 and holder 206 assembly are stored together prior to use, often in a storage solution of glutaraldehyde or other preservative. The parting sleeve 204 is preferably not pre-attached to the holder 206 to avoid causing any indentations in the leaflets 210 from long-term contact therewith. That is, the leaflets 210 are stored in their relaxed or coapted state.

FIG. 13B shows a preliminary step in preparing an aortic annulus AA for receiving the heart valve 200, including installation of guide sutures 230. The aortic annulus AA is shown schematically isolated and it should be understood that various anatomical structures are not shown for clarity. The annulus AA includes a fibrous ring of tissue that projects inward from surrounding heart walls. The annulus AA defines an orifice between the ascending aorta AO and the left ventricle LV. Although not shown, native leaflets projecting inward at the annulus AA to form a one-way valve at the orifice. The leaflets may be removed prior to the procedure, or left in place as mentioned above. If the leaflets are removed, some of the calcified annulus may also be removed, such as with a rongeur. The ascending aorta AO commences at the annulus AA with three outward bulges or sinuses, two of which are centered at coronary ostia (openings) CO leading to coronary arteries CA. As will be seen below, it is important to orient the prosthetic valve 208 so that the commissures 214 are not aligned with and thus not blocking the coronary ostia CO.

The surgeon attaches the guide sutures 230 at three evenly spaced locations around the aortic annulus AA. In the illustrated embodiment, the guide sutures 230 attach to locations below or corresponding to the coronary ostia CO (that is, two guide sutures are aligned with the ostia, and the third centered below the non-coronary sinus). The guide sutures 230 are shown looped twice through the annulus AA from the outflow or ascending aorta side to the inflow or ventricular side. Of course, other suturing methods or pledgets may be used depending on surgeon preference.

FIG. 13C shows the guide sutures 230 having been secured so that each extends in pairs of free lengths from the annulus AA and out of the operating site. The unitary heart valve 200 mounts on a distal section 240 of a delivery handle and the surgeon advances the valve into position within the aortic annulus AA along the guide sutures 230. That is, the surgeon threads the three pairs of guide sutures 230 through evenly spaced locations around the suture-permeable ring 216. If the guide sutures 230, as illustrated, anchor to the annulus AA below the aortic sinuses, they thread through the ring 216 mid-way between the valve commissure posts 214. The support structure 212 often includes an undulating shape of alternative commissures and cusps, and thus the guide sutures 230 pass through the suture-permeable ring 216 at the cusps of the valve. Furthermore, the exemplary ring 216 has an undulating inflow side such that the cusp locations are axially thicker than the commissure locations, which provides more material for securing the guide sutures 230.

Now with reference to FIG. 13D, the heart valve 200 rests in a desired implant position at the aortic annulus AA. The suture-permeable ring 216 desirably contacts the aortic side of the annulus AA, and is thus said to be in a supra-annular position. Such a position enables selection of a larger orifice prosthetic valve 200 in contrast to placing the ring 216, which by definition surrounds the valve orifice, within the annulus AA, or infra-annularly.

The surgeon delivers a plurality of suture snares 250 down each free length of the guide sutures 230 into contact with the upper or outflow side of the suture-permeable ring 216. The snares 250 enable downward pressure to be applied to the ring 216 and thus the valve 200 during the implant procedure, which helps insure good seating of the ring 216 on the annulus AA. The snares 250 also provide rigid enclosures around each of the flexible guide sutures 230 which helps avoid entanglement with the descending balloon catheter, as will be appreciated. As there are three guide sutures 230 and six free lengths, six snares 250 are utilized, though more or less is possible. The snares 250 are typically tubular straw-like members of medical grade plastic.

Figure 13F:
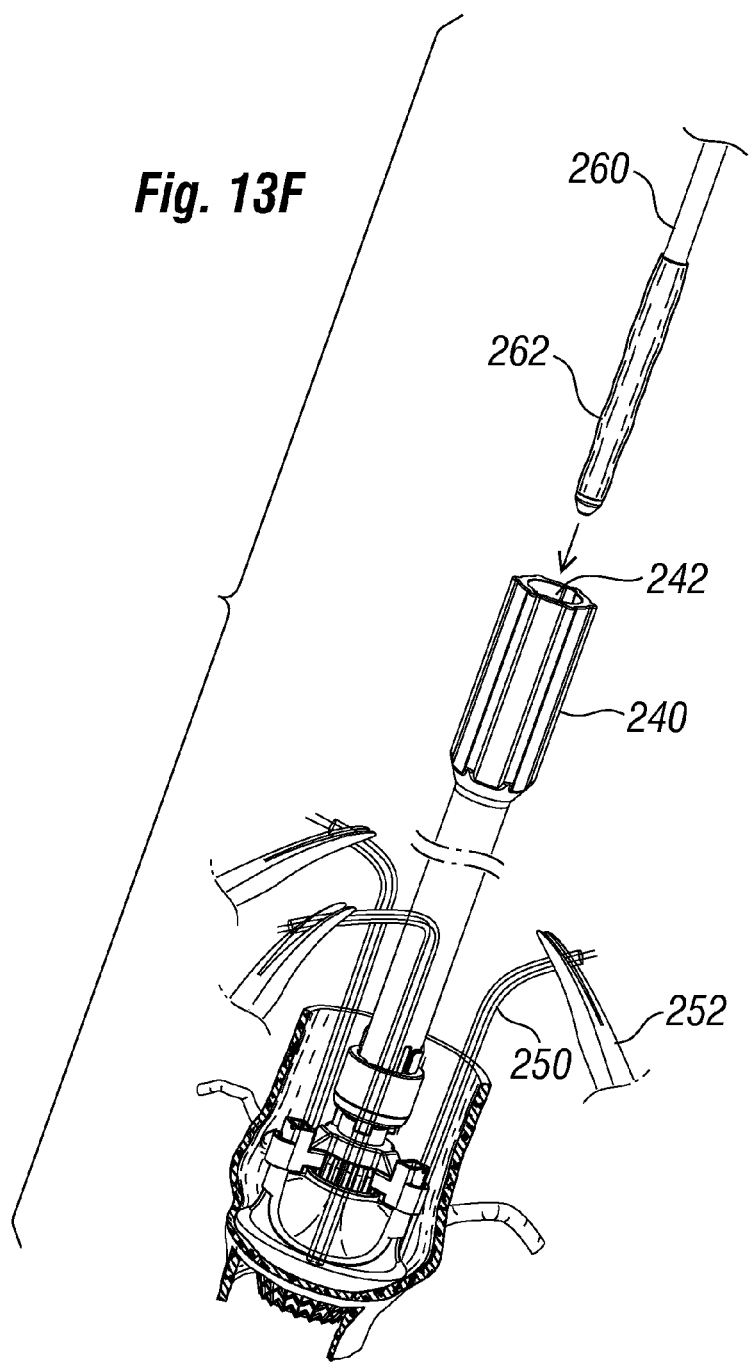

In FIG. 13E, forceps 252 are seen clamping upper ends of the suture snares 250, and bending one pair outward to improve access to the heart valve 200 and implant site. FIG. 13F shows all of the pairs of suture snares 250 bent outward prior to advancement of a balloon catheter 260. Although it will be described in greater detail below, the delivery system includes the aforementioned handle distal section 240 for manipulating the heart valve 200 on the holder 206. The distal section 240 is tubular and defines a lumen 242 for receiving the balloon catheter 260 having a balloon 262 in an uninflated state on a distal end thereof.

Figure 13G:
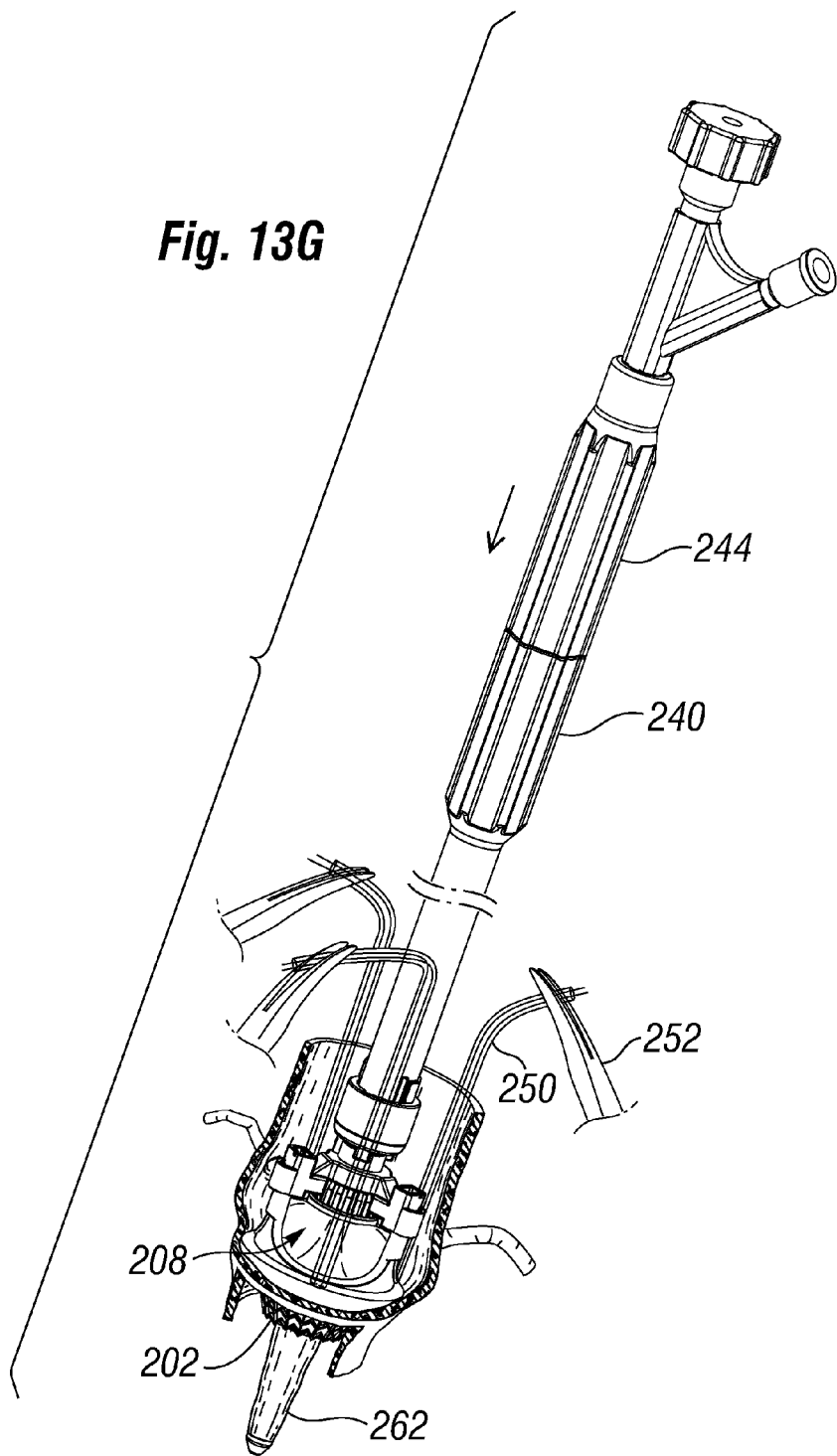

Now with reference to FIG. 13G, a delivery handle proximal section 244 is shown mated with the distal section 240, and the distal balloon 262 is shown extending beyond the coupling stent 202 of the heart valve 200 prior to inflation of the balloon.

FIGS. 13H and 13I show inflation and deflation of the balloon 262 of the balloon catheter 260, which plastically expands the coupling stent 202 against the annulus AA and a portion of the left ventricle LV. As will be explained further below, the balloon 262 expands with a conical exterior surface so that the lower second end 222 of the stent 202 expands outward wider than the first end. The resulting expanded stent 202 forms a frusto-conical surface.

Subsequently, the surgeon delivers three fastener clips 270 down the guide sutures 230 after removal of the snares 250, as seen in FIG. 13J. FIG. 13K shows the fully implanted unitary prosthetic heart valve 200 with the fastener clips 270 secured on the proximal face of the suture-permeable ring 216, and shows removal of the guide sutures 230. Any number of methods are available for securing the pairs of guide sutures 230 on the outflow side of the ring 216, including conventional knot-tying, however the fastener clips 270 are consistent with the overall aim of shortening the implant procedure. Inclusion of the guide sutures 230 primarily insures proper rotational orientation of the valve 200, as mentioned, but also helps secure the valve 200 in place at the annulus AA. That said, the guide sutures 230 may optionally be removed after delivery of the valve 200 so that the sole means of anchoring the valve is the expanded coupling stent 202. The latter option results in a true "knotless" valve attachment, if not completely sutureless.

The illustrated configuration with fastener clips 270 eliminates the need to tie suture knots, and the placement of the guide sutures 230 at the cusps of the native valve and prosthesis separates the clips from the commissures, thus increasing accessibility. Even if knots are used instead of the clips 270, the number of knots are reduced to three between the commissure posts, rather than multiple knots (12-24) as before, some of which were behind the commissure posts. The use of three sutures correctly positions the valve 200 and centering the sutures between the commissure posts is the most accessible for tying knots because the cusps are the lowest points in the annulus. Placement of knots (or clips) at the lowest point in the annulus also helps minimize the risk of coronary occlusion.

A more detailed understanding of the unitary heart valve 200 and holder 206 follows with reference to FIGS. 14-19. With reference to FIGS. 14 and 15, the heart valve 200 including the prosthetic valve 208 and coupling stent 202 is shown attached to the holder 206, while the holder is shown by itself in FIG. 16. The assembly is also seen in FIGS. 17A-17E.

As explained above, the prosthetic valve 208 has three flexible leaflets 210 supported by a non-expandable, non-collapsible annular support structure 212 and a plurality of commissure posts 214 projecting in an outflow direction, with a suture-permeable ring 216 circumscribing an inflow end thereof. In one embodiment, the heart valve 200 is a commercially available, non-expandable prosthetic heart valve 208 having a sewing ring 216, such as a Carpentier-Edwards PERIMOUNT Magna Aortic Bioprosthesis valve, attached to a pre-crimped tapered Stainless Steel coupling stent 202 lined and/or covered by a fabric (e.g., Dacron) skirt 218, as seen in FIG. 15. An external fabric cover or sleeve is shown below with reference to the detailed stent drawings of FIGS. 18-19.

As seen in FIG. 16, the holder 206 includes a central tubular body having the downwardly-directed boss 226 on the lower end, an upwardly directed hub 227 on the upper end, a narrow tubular section 228 below the hub, and section with three outwardly-directed anchoring fingers 229 (see FIG. 14). A continuous cylindrical lumen extends the length of the holder 206 from top to bottom for passage of the distal end of the balloon catheter 260, as mentioned above. The fingers 229 include anchoring structure as will be described that permits attachment to each of the upstanding commissure posts 214 on the prosthetic valve 208.

FIG. 16 illustrates the downwardly-directed boss 226 having external threading for mating with the leaflet parting sleeve 204. Three gaps 231 separate the boss 226 from downwardly-extending portions of each anchoring finger 229 and provide annular clearance for the tubular sleeve 204. Small ratchet teeth 232 provided on an inner surface of each anchoring finger 229 contact the exterior of the parting sleeve 204, and preferably a roughened portion thereof, and provide an anti-rotation friction to secure the sleeve on the boss. The teeth 232 are each cantilevered inward in a clockwise direction looking from the bottom so as to permit the sleeve 204 to easily screw on but present resistance to unscrewing the sleeve in a counter-clockwise direction.

Each anchoring finger 229 includes a generally flat lower face 233 bordered on an outer edge by a downwardly-extending U-shaped rail 234. A plurality of through holes 235 extend axially through each finger 229 to an upper surface, as seen in FIG. 17D. In particular, a first pair of through holes 235a opens radially inward from an upper cutting guide 236, and a second pair of through holes 235b opens radially outward from the cutting guide. As seen best in FIG. 15, the tip of each commissure post 214 contacts the lower face 233 of one of the anchoring fingers 229 within the U-shaped rail 234. The commissure post 214 is preferably fabric-covered, or otherwise suture-permeable, and a suture (not shown) is used to secure the post 214 to the underside of the anchoring finger 229. The suture passes through the first and second pairs of through holes 235a, 235b such that a mid-portion extends across spaced notches 237 in the cutting guide 236 (see FIG. 17D again). By securing the free ends of the suture to the holder 206, such as on the underside of the fingers 229, a scalpel may be used to sever the mid-portion that extends across a cutting well 238 in the cutting guide 236 to release the commissure post 214 from the holder. Severing all three sutures releases the prosthetic valve 208 from the holder 206.

FIGS. 17A-17F illustrate a preferred suture-permeable ring 216 circumscribing an inflow end of the prosthetic valve 208. The ring 216 defines a relatively planar upper face 239 and an undulating lower face 241. Cusps of the annular support structure 212 abut the upper face 239 opposite locations where the lower face 241 defines peaks. Conversely, the valve commissure posts 214 align with locations where the lower face 241 defines troughs. The undulating shape of the lower face 241 advantageously matches the anatomical contours of the aortic side of the annulus AA, that is, the supra-annular shelf. The ring 216 preferably comprises a suture-permeable material such as rolled synthetic fabric or a silicone inner core covered by a synthetic fabric. In the latter case, the silicone may be molded to define the contour of the lower face 241 and the fabric cover conforms thereover.

The coupling stent 202 (shown separated in FIGS. 18-19) preferably attaches to the suture-permeable ring 216 during the manufacturing process in a way that preserves the integrity of the ring and prevents reduction of the valve's effective orifice area (EOA). Desirably, the coupling stent 202 will be continuously sutured to the ring 216 in a manner that maintains the contours of the ring. In this regard, sutures may be passed through apertures or eyelets 243 arrayed along an upper or first end 245 of the stent 202. Other connection solutions include prongs or hooks extending inward from the stent, ties, Velcro, snaps, adhesives, etc. Alternatively, the coupling stent 202 may be more rigidly connected to rigid components within the prosthetic valve 208.

The plastically-expandable coupling stent 202 is seen in greater detail in a contracted state in FIGS. 18A-18C, and in an expanded state in FIGS. 19A-19D. The general function of the stent 202 is to provide the means to attach the prosthetic valve 208 to the native aortic root. This attachment method is intended as an alternative to the present standard surgical method of suturing aortic valve bio-prostheses to the aortic valve annulus, and is accomplished in much less time. Further, this attachment method improves ease of use by eliminating most of not all suturing.

Device attachment to the native valve structure is achieved using a balloon catheter to expand and deploy the stent covered by a fabric (e.g., Dacron) skirt 218. In the views of FIGS. 17F and 18-19, the fabric skirt 218 surrounds the outside of the stent 202, and is shown in phantom, but may also be provided on the inside of the stent. The main functions of this sleeve 218 are to help prevent paravalvular leaks and provide means to securely encapsulate any Calcium nodules on the aortic valve leaflets (if left in place) and/or the aortic valve annulus.

As best seen in FIG. 17F, a preferred embodiment of the valve 200 includes a fabric sleeve 218 covering the entire inflow coupling stent 202 with a combination of PTFE knit cloth on the ID, ends and part of the OD. The part of the OD closest to the sewing ring 216 is also covered with a PET knit cloth to seal leaks. Covering the entire coupling stent 202 eliminates exposed metal and decreases the risk of thromboembolic events and abrasion.

The stent 202 may be similar to an expandable Stainless Steel stent used in the Edwards SAPIEN Transcatheter Heart Valve. However, the material is not limited to Stainless Steel, and other materials such as Co—Cr alloys, etc. may be used.

FIGS. 18A-18C show the stent 202 in its pre-crimped tapered configuration that facilitates insertion through the calcified native aortic valve (see FIG. 13C). The stent lower edge 222 describes a circle having a smaller diameter than a circle described by the upper or first end 245. The upper end 245 follows an undulating path with peaks and troughs that generally corresponds to the undulating contour of the underside 241 of the suture-permeable ring 216 (see FIG. 15). The mid-section of the stent 202 is somewhat similar to the stent 140 seen in FIG. 12B, and has three rows of expandable struts 246 in a sawtooth pattern between axially-extending struts 247, and a thicker wire upper end 245. The axially-extending struts 247 are in-phase with the peaks and troughs of the upper end 245 of the stent. The reinforcing ring defined by the upper end 245 is continuous around its periphery and has a substantially constant thickness or wire diameter interrupted by the aforementioned eyelets 243.

The minimum I.D. of the upper end 245 of the covered stent 202 will always be bigger than the I.D. of the prosthetic valve 208 to which it attaches. For instance, if the upper end 245 secures to the underside of the suture-permeable ring 216, which surrounds the support structure 212 of the valve, it will by definition be larger than the I.D. of the support structure 212.

FIGS. 19A-19C show the stent 202 in its expanded configuration that anchors the heart valve 200 to the calcified native aortic valve (see FIG. 13K). The stent lower end 222' is seen in FIG. 19C expanded from its contracted dimension of FIG. 18C. Note that the shape is not precisely circular, and use of the term "diameter" to define the contracted and expanded sizes is necessarily approximate. As will be explained below, the procedure desirably incorporates a shaped expansion balloon 262 that expands the stent 202 from its initial conical shape of FIG. 18A to its final conical shape of FIG. 19A. In the expansion step, the balloon 262 primarily exerts greater outward force on the lower portions of the stent 202, so that the upper end 245 remains substantially the same. This prevents distortion of the suture-permeable ring 216 to which the stent 202 attaches.

It should be noted that a plastically-expandable stent 202 desirably provides sufficient anchoring force for the heart valve 200, and also permits some expansion of the annulus itself. That said, a self-expanding material may be used, though such a stent would likely require supplemental coupling means, such as barbs, staples, etc.

Figure 20A:
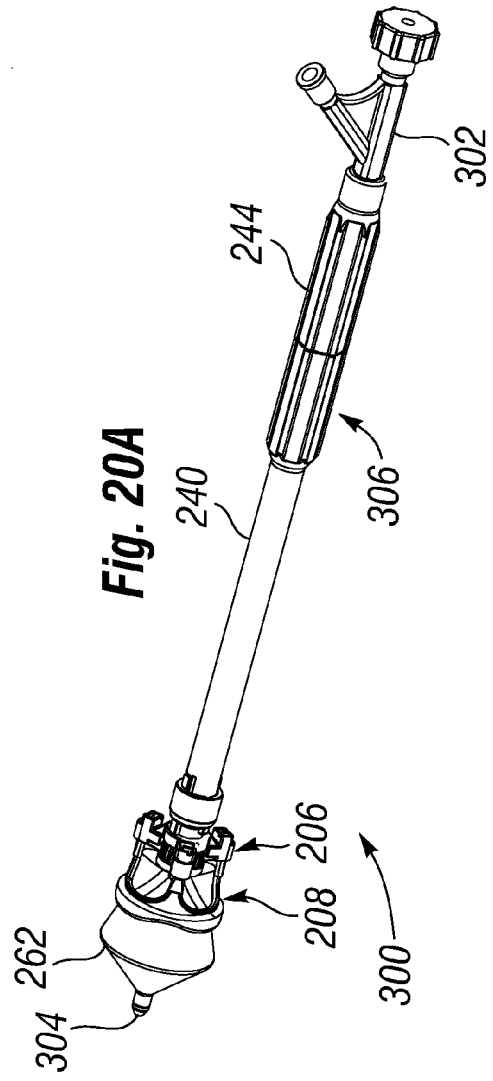
FIGS. 20A-20C are perspective, elevational and longitudinal sectional views of a system for delivering the heart valve of FIGS. 14-17 showing a balloon on a balloon catheter in an inflated configuration and omitting the coupling stent of the heart valve.
Figure 20B:
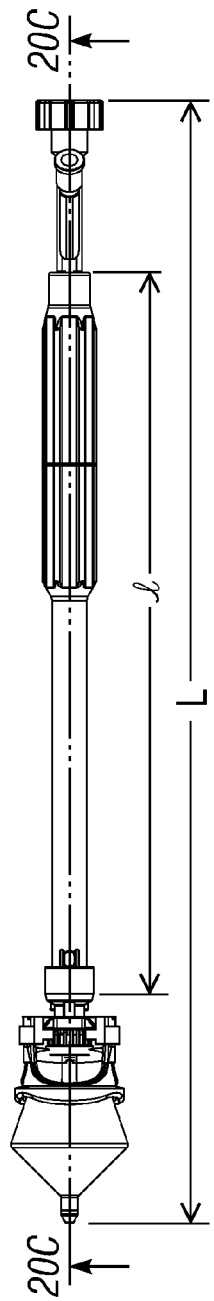
Figure 20C:
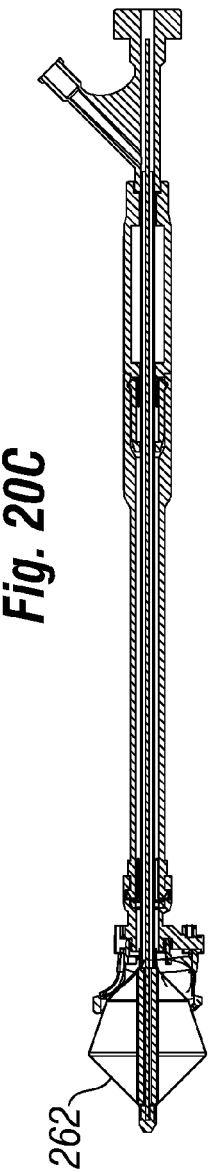
Figure 23:
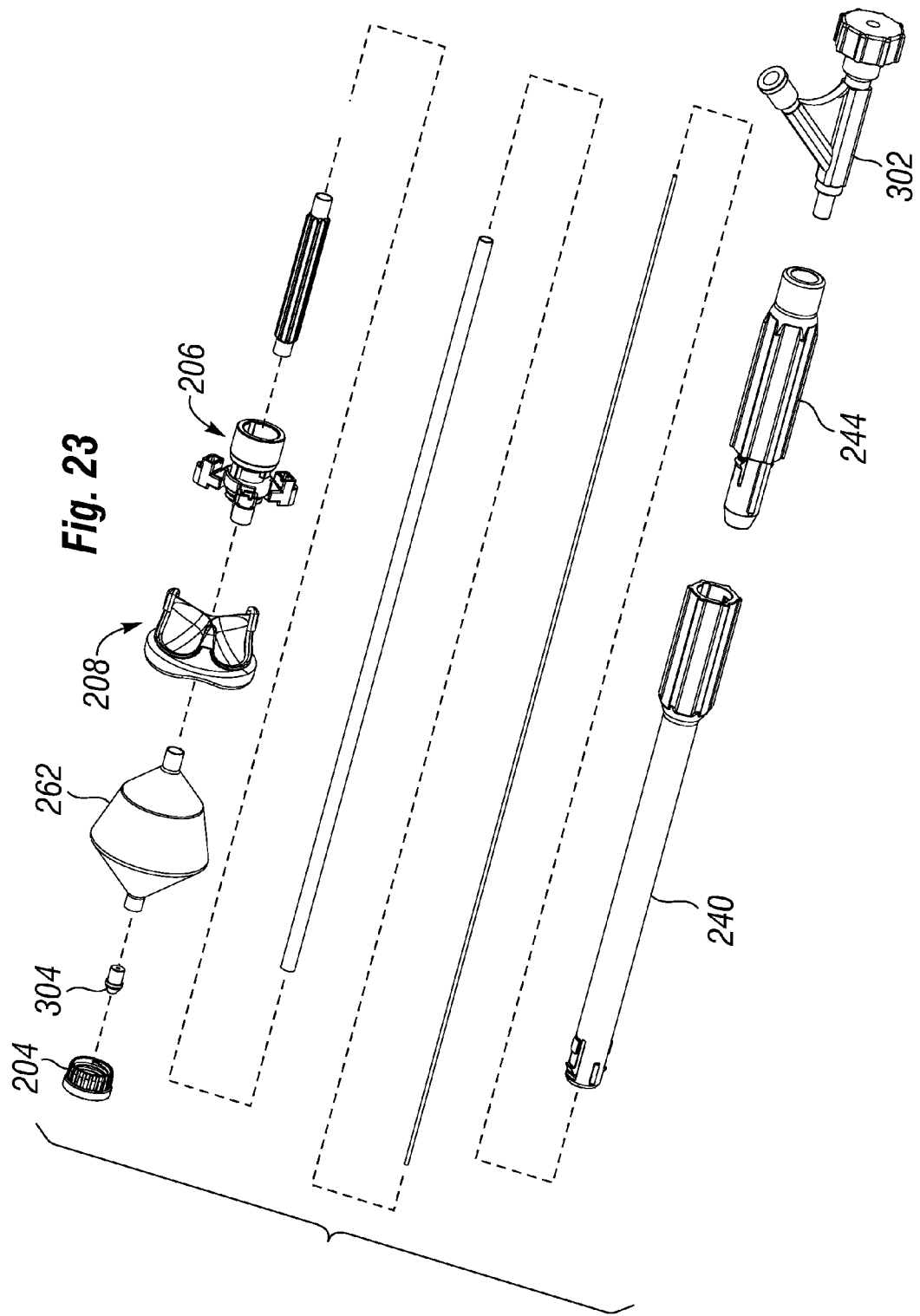
FIG. 23 is an exploded perspective view of the delivery system of FIGS. 20A-20C, heart valve and holder.
Figure 26A:
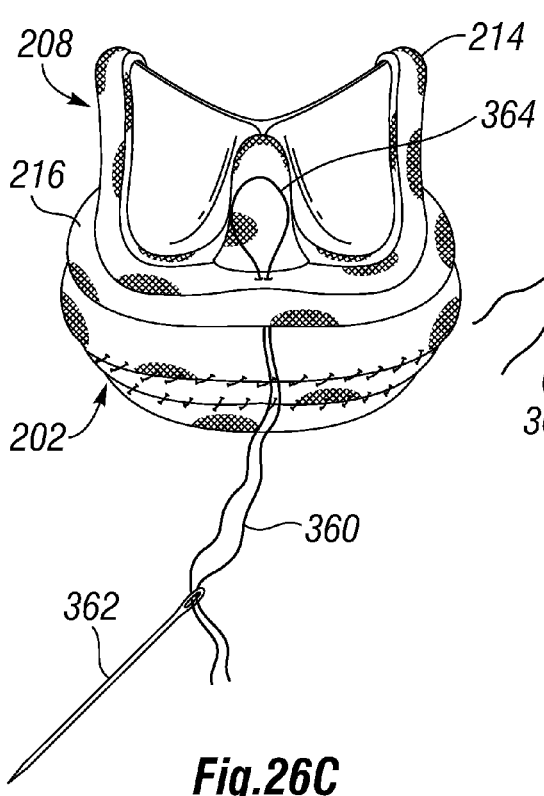
Figure 26B:
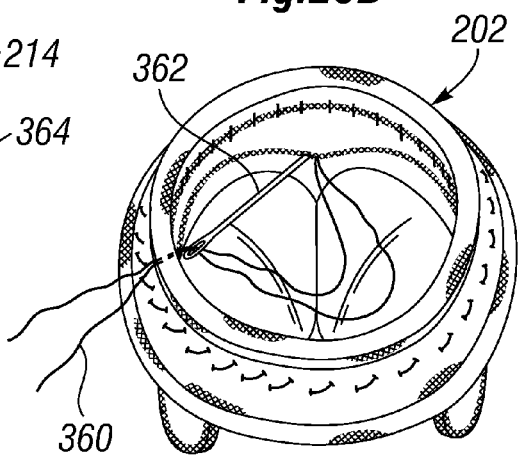
Figure 26C:
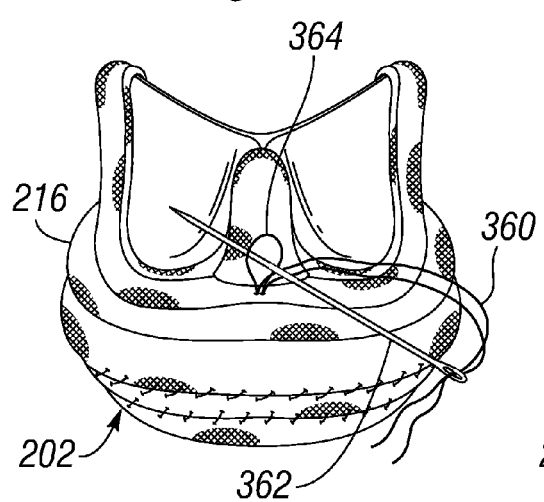
Figure 26D:
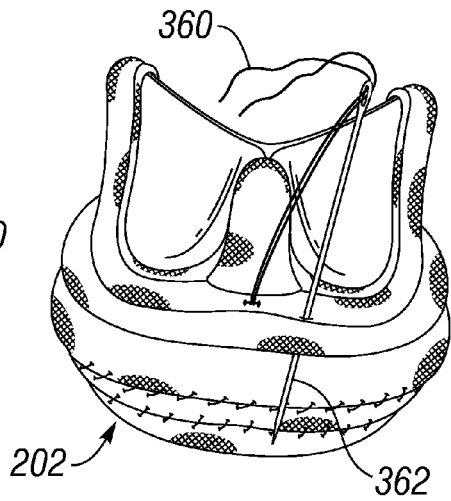

FIGS. 20A-20C show a system 300 for delivering the unitary heart valve 200 of FIGS. 14-17. The delivery or deployment system 300 consists of a two-piece handle, wherein one piece is removable and hollow and used as a handle interface with the bio-prosthesis.

The system 300 in FIGS. 20A-20C is illustrated with the prosthetic valve 208 attached to the holder 206, but omits the coupling stent 202 for clarity in viewing and understanding the function of the balloon 262. The system 300 includes the aforementioned balloon catheter 260 which commences on a proximal end with a Y-fitting 302 and terminates at a distal tip 304. The balloon catheter 260 extends the entire length of the system 300 and will be described further below with reference to FIGS. 24A-24D. The entire system preferably has a length L from the proximal end of the Y-fitting 302 to the distal tip 304 of between about 100 and 500 mm.

The present application describes an essentially rigid delivery system in that the handle 306 is preferably made of rigid polymer such as polypropylene. An alternative system contemplates a flexible delivery system that may be bent out of the way and have a length of up to 800 mm. The diameter of such a delivery system will not be as small as previous percutaneous devices, as the primary access route is through a direct access pathway and small diameters are not necessary.

The system 300 also includes a two-piece handle assembly 306 that combines the aforementioned distal section 240 mated with the proximal section 244. The handle components are further described with reference to FIGS. 21 and 22. The length l of the handle 306 is preferably between about 150 and 300 mm. The Y-fitting 302 connected in series to the proximal handle section 244, which in turn couples to the distal section 240 attached to the holder 206. A through lumen extends the length of these connected components for sliding passage of the balloon catheter 260 such that the balloon 262 may extend through the prosthetic valve 208. The connections between the components comprise concentric tubular couplings wherein a distal tube fits within a proximal tube to reduce the chance of snagging the balloon 262 as it travels therethrough.

FIG. 21 is an elevational view of the delivery system 300 of FIGS. 20A-20C including the coupling stent 202, while FIG. 22 shows the components exploded, but without the balloon catheter 260, valve 200 and holder 206. The distal and proximal handle sections 240, 244 include snap-fit couplers 310 on their mating ends in the form of cantilevered teeth that snap into complementary recesses formed in respective receiving apertures (one of which is on the hub 227 of the valve holder 206). Of course, threading on the mating parts could also be used, as well as other similar expedients. The distal handle section 240 includes a proximal grip 312 that facilitates manipulation of the heart valve 200 when attached thereto. Likewise, the proximal handle section 244 has an exterior grip 314 to enable a user to easily couple and decouple it with respect to the adjacent components, and also to provide continuity with the distal section grip 308.

FIG. 21 shows the balloon 262 inflated to expand the valve coupling stent 202, while FIGS. 23 and 24A-24D show the preferred shape of the balloon 262. As mentioned, the final or expanded shape of the coupling stent 202 is frustoconical, and the balloon 262 includes an up-tapered middle segment 320 that contacts the coupling stent 202. The middle segment 320 has the same or a slightly greater included taper angle θ to account for material rebound. As seen in FIG. 24D, the taper angle θ is preferably between about 0-45°, and more preferably is about 38° (0° being a cylindrical expansion). A short proximal lead-in up-taper 322 and a distal down-taper 324 flank the up-tapered middle segment 320. Alternatively, the balloon 262 may include curves or non-axi-symmetric contours to deform the coupling stent 202 to various desired shapes to fit better within the particular annulus. Indeed, various potential shapes are described in U.S. Patent Publication 2008-0021546, entitled System for Deploying Balloon-Expandable Heart Valves, published Jan. 24, 2008, the disclosure of which is expressly incorporated herein.

In use, the prosthetic heart valve 200 (or valve 30) is selected based on type and size. Typically, the heart valve 200 includes bioprosthetic leaflets, such as bovine pericardium leaflets, and remains stored in a preservative solution in a contaminant-free jar. If the holder 206 attaches to the valve with sutures, as preferred, the holder also resides in the jar during storage and shipping.

After the surgeon stops the heart and exposes and measures the annulus for size, he/she selects a valve size that is larger than the annulus. Technicians open the jar containing the selected valve and snap the distal handle section 240 into the holder hub 227 while the combination of the heart valve 200 and holder 206 is still in the jar. The resulting assembly facilitates handling of the bio-prosthesis during pre-procedure preparations (i.e. rinsing steps, etc.). The grip 312 on the distal handle section 240 facilitates these preparation steps.

The surgeon places guiding sutures 230 into the annulus at the cusp locations, and then back out and through the valve sewing ring in the corresponding locations. The surgeon slides the valve down the guiding sutures 230 using the distal end 240 of the handle assembly 306 to press the valve into position within the annulus, as seen in FIG. 13C. The guiding sutures 230 facilitate rotational and axial positioning of the valve 200 so the valve does not block the coronary ostia and sits down against the top of the annulus, as seen in FIG. 13D. After the valve 200 is secured in position by the guiding sutures 230 and snares 250, as in FIG. 13E, the surgeon places the balloon catheter 260 (see FIG. 13F) through the distal section 240 and locks it into position using the proximal section 244, as shown in FIG. 13G. The surgeon then inflates the balloon 262, as shown in FIG. 13H, expanding the coupling stent 202 which expands the annulus and secures the valve 200 in the correct position. After balloon deflation, as shown in FIG. 13I, the surgeon separates the holder 206 from the valve 200, and withdraws the holder, handle assembly 306, and balloon catheter 260 from the patient using the grips 312, 314 (see FIG. 22) on the handle.

In the case of the first embodiment, where the unitary heart valve 30 mounts on a balloon catheter 32, the proximal section 62 that incorporates the balloon 40 pre-assembled in its central lumen snaps onto the distal section 64 to form the hollow handle 60. As both handle pieces are snapped together, the balloon catheter with its wrapped balloon is encapsulated in the handle shaft formed by the two mating handle pieces.

The delivery system 300 provides two positions for the balloon catheter:

i. A retracted balloon position used at the pre coupling stent deployment stage of the procedure.

ii. An advanced balloon position used for coupling stent deployment. The advanced position is used once the heart valve 200 has been placed in the desired aortic root position and balloon expansion is required to expand the coupling stent and secure the implant in place.

When proper placement of the valve 200 is insured, the surgeon inflates the balloon 262 using saline or similar expedient to its maximum size, or with a predetermined volume of inflation fluid. This expands the coupling stent 202 to its implant size against the annulus (or leaflets). Thereafter, the balloon 262 is deflated and removed from within the heart valve 200. Upon completing deployment, the valve holder sutures are cut with a scalpel and the delivery system 300 retracted through valve leaflets to complete the deployment procedure.

In another advantageous feature, the two-component valve system illustrated in the preceding figures provides a device and method that substantially reduces the time of the surgical procedure as compared with replacement valves that are sutured to the tissue after removing the native leaflets. For example, the coupling stent 36, 202 may be deployed quickly such that the heart valve 200, 30 may be rapidly attached to the annulus. This reduces the time required on extracorporeal circulation and thereby substantially reduces the risk to the patient.

In addition to speeding up the implant process, the present invention having the valve and its robust plastically-expandable stent, permits the annulus to be expanded to accommodate a larger valve than otherwise would be possible. In particular, clinical research has shown that the left ventricular outflow tract (LVOT) can be significantly expanded by a balloon-expandable stent and still retain normal functioning. In this context, "significantly expanding" the LVOT means expanding it by at least 5%, more preferably between about 5-30%, and typically between 10-20%. In absolute terms, the LVOT may be expanded 1.0-5 mm depending on the nominal orifice size. This expansion of the annulus creates an opportunity to increase the size of a surgically implanted prosthetic valve. The present invention employs a balloon-expandable valve stent which permits expansion of the LVOT at and just below the aortic annulus, at the inflow end of the prosthetic valve. The interference fit created between the outside of the coupling stent and the LVOT secures the valve, desirably without pledgets or sutures taking up space, thereby allowing for placement of the maximum possible valve size. A larger valve size than would otherwise be available with conventional surgery enhances volumetric blood flow and reduces the pressure gradient through the valve.

It will be appreciated by those skilled in the art that embodiments of the present invention provide important new devices and methods wherein a valve may be securely anchored to a body lumen in a quick and efficient manner. Embodiments of the present invention provide a means for implanting a prosthetic valve in a surgical procedure with as few as three sutures rather than the 12-24 sutures typically used for aortic valve replacement. Accordingly, the surgical procedure time is substantially decreased. Furthermore, in addition to providing a coupling stent for the valve, the stent may be used to maintain the native valve in a dilated condition. As a result, it is not necessary for the surgeon to remove the native leaflets, thereby further reducing the procedure time.

It will also be appreciated that the present invention provides an improved system wherein a valve member may be replaced in a more quick and efficient manner. More particularly, it is not necessary to cut any sutures in order to remove the valve. Rather, the valve member may be disconnected from the coupling stent and a new valve member may be connected in its place. This is an important advantage when using biological tissue valves or other valves having limited design lives.

The variations on quick-connect heart valves, systems and methods may change based on surgeon preferences, empirical testing, economies, etc. Several possible variations include:
  A stent frame that provides attachment means and also prevents native, calcified leaflets to interfere with flow.
  A secondary piece mounted on the aortic side of the suturing ring to help improve attachment.

The present application encompasses numerous ways to couple the prosthetic valve 208 to the coupling stent 202, as mentioned above. However, a preferred version includes attaching the coupling stent 202 to the inflow end of valve 208 with sutures, as will be described with reference to FIGS. 25-28.

FIG. 25A shows the valve 208 slightly separated above the coupling stent 202 with a first temporary suture 350 connected therebetween. The first temporary suture 350 includes a triple wrap loop with suture material (e.g., P/N 400830001) which passes downward from the top of the sewing ring 216, at the center of the commissure 214, between the sewing ring and synthetic support structure 212 (e.g., Elgiloy band, not shown) of the valve 208. The needle 352 threads down through the sewing ring 216 toward inflow end of the valve 208, through a commissure hole 354 on the coupling stent 202 (shown schematically in FIG. 25B) to the inside of the stent, and back upward through the sewing ring 216 through the triple wrap loop to be tightened. The technician then makes one backstitch on the rolled tab on the stent 202 and trims the loose ends off. Three such temporary sutures 350 are installed at the three commissures of the valve 208. These three sutures are used to position the stent 202 below the valve 208 while permanent sutures are installed.

Note that in this version the upper end 245 of the stent 202 follows an undulating path with peaks and troughs that generally corresponds to the undulating contour of the underside of the sewing ring 216. Therefore, the temporary sutures 350 ensure that the peaks of the upper end 245 of the stent 202 match the troughs of the sewing ring 216, which are located under the commissures 214 of the valve.

FIGS. 26A-26D illustrate several initial steps in an exemplary installation of permanent sutures 360. Preferably, the technician cuts a length of suture material (e.g., PTFE thread, P/N 491176003) approximately 30 inches long and double threads a needle 362. Starting at a commissure center, and between the sewing ring and Elgiloy band, place the needle 362 down through the sewing ring 216 toward inflow end. Go through the commissure hole 354 on the coupling stent 202 (FIG. 25B) to the inside of the stent and back up through the sewing ring 216, through the suture loop 364 and tighten. Go back down through sewing ring 216, catch the stent 202 between the commissure strut hole 354 and the next vertical strut hole 356 (FIG. 25B), to the inside of the stent and back up through the sewing ring to catch the previous stitch and tighten. Once the next commissure hole is reached, remove the temporary stitch 350.

Continue the stitches at every stent hole and the between every stent hole making 36 stitches, as illustrated in FIGS. 27 and 28. In the illustrated embodiment, the stent 202 has eighteen holes along the upper end 245, three commissure holes 354 at the peaks and five intermediate holes 356, as seen in FIG. 25B. Of course, the stent 202 may have more or less holes, or no holes, though the holes provide secure anchorages, clear spacing, and good targets for the assembly technician. The technician completes the stitch by passing the suture 360 through the starting commissure hole again, catching the first stitch and making a single lock knot. The suture 360 is then moved to the rolled tab on the stent 202 and another double-spaced single lock knot is made. The technician buries the suture 360 and cuts the thread. No gap is left between the stitches on the sewing ring 216 area, as seen in FIG. 29. No gap is left between sewing ring 216 and the stent 202.

While the invention has been described in its preferred embodiments, it is to be understood that the words which have been used are words of description and not of limitation. Therefore, changes may be made within the appended claims without departing from the true scope of the invention.

What is claimed is:

1. A system for delivering a prosthetic heart valve, comprising:
  a heart valve including a prosthetic valve having a non-expandable, non-collapsible orifice defined by a support structure with an undulating shape of alternative commissures and cusps in an outflow direction that supports flexible leaflets that come together within the orifice in an outflow direction, the heart valve further including an expandable coupling stent extending from an inflow end thereof, the coupling stent having a contracted state for delivery to an implant position and an expanded state;

a valve holder connected to an outflow end of the heart valve and having a sleeve extending between the flexible leaflets, the holder and sleeve together defining a throughbore from an outflow side of the leaflets to an inflow side;

a balloon catheter having a balloon; and a handle configured to attach to a proximal end of the valve holder and having a lumen for passage of the balloon catheter, the lumen aligned with the throughbore of the valve holder and sleeve, the balloon extending distally through the handle lumen and the throughbore and distally between the heart valve leaflets without contacting the leaflets such that the balloon is positioned to expand the coupling stent.

2. The system of claim 1, wherein the prosthetic valve includes a sewing ring on the inflow end thereof, and wherein the coupling stent attaches to the sewing ring.

3. The system of claim 2, wherein the coupling stent includes a reinforcing ring on an outflow end continuously sewn to the sewing ring and a plurality of interconnected expandable struts extending therefrom that are deformed by the balloon from the contracted state to the expanded state.

4. The system of claim 3, wherein the reinforcing ring follows an undulating path with peaks and troughs that generally corresponds to an undulating contour of an underside of the sewing ring.

5. The system of claim 1, wherein the contracted state of the coupling stent is conical, tapering down in a distal direction.

6. The system of claim 1, wherein the handle comprises a proximal section and a distal section that may be coupled together in series to form a continuous lumen, and wherein the distal section is adapted to couple to a central hub of the holder to enable manual manipulation of the heart valve using the distal section prior to connection with the proximal handle section.

7. The system of claim 6, wherein the balloon catheter and proximal handle section are packaged together with the balloon within the proximal section lumen.

8. The system of claim 1, wherein the heart valve mounted on the holder is packaged separately from the handle and the balloon catheter.

9. The system of claim 1, wherein the sleeve comprises a separate element threaded to the valve holder.

10. The system of claim 9, wherein the heart valve mounted on the holder is packaged separately from the sleeve.

11. The system of claim 1, wherein the handle attaches to a proximal end of the valve holder with a snap-fit coupling.

12. A system for delivering a prosthetic heart valve, comprising:

a heart valve including a prosthetic valve defined by a support structure with an undulating shape of alternative commissures and cusps in an outflow direction that supports flexible leaflets that come together within a flow orifice in the outflow direction, the heart valve further including a balloon-expandable coupling stent attached to and extending from an inflow end thereof, the coupling stent having a contracted state for delivery to an implant position and an expanded state;

a valve holder and handle system connected to an outflow end of the heart valve and having a throughbore that extends from an outflow side to an inflow side of the leaflets; and a balloon catheter having a balloon that passes distally through the throughbore of the valve holder and handle system and distally past without contacting the heart valve leaflets such that the balloon is positioned to expand the coupling stent.

13. The system of claim 12, wherein the contracted state of the coupling stent is conical, tapering down in a distal direction.

14. The system of claim 12, wherein the valve holder and handle system comprises a valve holder connected to the outflow end of the heart valve, a sleeve that connects to the valve holder and extends between the flexible leaflets, and a handle configured to attach to a proximal end of the valve holder and having a lumen for passage of the balloon catheter.

15. The system of claim 14, wherein the sleeve is threaded to the valve holder.

16. The system of claim 14, wherein the heart valve mounted on the holder is packaged separately from the sleeve.

17. The system of claim 14, wherein the handle attaches to a proximal end of the valve holder with a snap-fit coupling.

18. The system of claim 12, wherein the prosthetic valve includes a sewing ring on the inflow end thereof, and the coupling stent is continuously sewn to the sewing ring.

19. The system of claim 18, wherein the coupling stent includes a reinforcing ring on an outflow end sewn to the sewing ring and a plurality of interconnected expandable struts extending therefrom that are deformed by the balloon from the contracted state to the expanded state.

20. The system of claim 19, wherein the reinforcing ring follows an undulating path with peaks and troughs that generally corresponds to an undulating contour of an underside of the sewing ring.

21. A system for delivering a prosthetic heart valve, comprising:

a heart valve including a prosthetic valve having a support structure that supports flexible leaflets that coapt in an outflow direction to provide a one-way valve, the heart valve further including a balloon-expandable coupling stent attached to and extending from an inflow end thereof, the coupling stent having a contracted state for delivery to an implant position and an expanded state;

a valve holder connected to an outflow end of the heart valve;

a sleeve connected to the valve holder and extending distally therefrom within the flexible leaflets, the sleeve having a throughbore; and a balloon catheter mounted to slide within a lumen of a delivery handle that mates with a proximal end of the valve holder such that a user can advance a balloon on the balloon catheter distally through the valve holder and sleeve past the heart valve leaflets such that the balloon is positioned to expand the coupling stent.

22. The system of claim 21, wherein the contracted state of the coupling stent is conical, tapering down in a distal direction.

23. The system of claim 21, wherein the sleeve is threaded to the valve holder.

24. The system of claim 21, wherein the heart valve connected with the holder is packaged separately from the sleeve.

25. The system of claim 21, wherein the delivery handle mates with the proximal end of the valve holder with a snap-fit coupling.

26. The system of claim 21, wherein the prosthetic valve includes a sewing ring on the inflow end thereof, and the coupling stent is continuously sewn to the sewing ring.

27. The system of claim 26, wherein the coupling stent includes a reinforcing ring on an outflow end sewn to the sewing ring and a plurality of interconnected expandable struts extending therefrom that are deformed by the balloon from the contracted state to the expanded state.

28. The system of claim 27, wherein the reinforcing ring follows an undulating path with peaks and troughs that generally corresponds to an undulating contour of an underside of the sewing ring.

* * * * *